United States Patent
Ma et al.

(10) Patent No.: US 10,240,001 B2
(45) Date of Patent: Mar. 26, 2019

(54) O-HYDROXY-FUNCTIONALIZED DIAMINES, POLYIMIDES, METHODS OF MAKING EACH, AND METHODS OF USE

(71) Applicant: KING ABDULLAH UNIVERSITY OF SCIENCE AND TECHNOLOGY, Thuwal (SA)

(72) Inventors: Xiaohua Ma, Thuwal (SA); Bader S. Ghanem, Thuwal (SA); Ingo Pinnau, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 24 days.

(21) Appl. No.: 15/325,926

(22) PCT Filed: Jul. 14, 2015

(86) PCT No.: PCT/IB2015/001396
§ 371 (c)(1),
(2) Date: Jan. 12, 2017

(87) PCT Pub. No.: WO2016/009273
PCT Pub. Date: Jan. 21, 2016

(65) Prior Publication Data
US 2017/0190842 A1 Jul. 6, 2017

Related U.S. Application Data

(60) Provisional application No. 62/024,487, filed on Jul. 15, 2014.

(51) Int. Cl.
*B01D 53/22* (2006.01)
*B01D 71/64* (2006.01)
(Continued)

(52) U.S. Cl.
CPC ....... *C08G 73/1085* (2013.01); *B01D 53/228* (2013.01); *B01D 71/64* (2013.01);
(Continued)

(58) Field of Classification Search
CPC .. B01D 53/228; B01D 67/0006; B01D 71/64; B01D 2325/20; C08G 73/1067; C08G 73/1085; C07C 213/02; C07C 215/88
See application file for complete search history.

(56) References Cited

U.S. PATENT DOCUMENTS 9,266,058 B1 * 2/2016 Liu ................. B01D 53/228
9,751,985 B2 * 9/2017 Ghanem ............ C08G 73/1085
(Continued)

FOREIGN PATENT DOCUMENTS

WO    WO2014207559 A2    12/2014

OTHER PUBLICATIONS

Kim, Yun-Hi et al., "Synthesis and Characterization of Highly Soluble and Oxygen Permeable New Polyimides Based on Twisted Biphenyl Dianyhdride and Spirobifluorene Diamine", Macromolecules, 2005, 38, pp. 7950-7956. (Year: 2005).*
(Continued)

*Primary Examiner* — Jason M Greene
(74) *Attorney, Agent, or Firm* — Billion & Armitage; Lisbeth C. Robinson

(57) ABSTRACT

Embodiments of the present disclosure provide for an ortho (o)-hydroxy-functionalized diamine, a method of making an o-hydroxy-functionalized diamine, an o-hydroxy-functionalized diamine-based polyimide, a method of making an o-hydroxy-functionalized diamine imide, methods of gas separation, and the like.

19 Claims, 10 Drawing Sheets

$^1$H NMR of the monomer and polymers, DMSO-$d_6$ was used as solvent.

TGA curve of the pristine and thermal rearranged polymer membranes

(51) Int. Cl.
*C08G 73/10* (2006.01)
*C07C 213/02* (2006.01)
*C07C 215/88* (2006.01)
*C08G 73/22* (2006.01)

(52) U.S. Cl.
CPC .......... *C07C 213/02* (2013.01); *C07C 215/88* (2013.01); *C08G 73/1067* (2013.01); *C08G 73/22* (2013.01); *B01D 2256/12* (2013.01); *B01D 2256/16* (2013.01); *B01D 2256/18* (2013.01); *B01D 2256/245* (2013.01); *B01D 2257/102* (2013.01); *B01D 2257/504* (2013.01); *B01D 2257/7022* (2013.01); *B01D 2325/20* (2013.01); *C07C 2103/90* (2013.01); *C07C 2103/97* (2013.01); *Y02C 10/10* (2013.01); *Y02P 20/132* (2015.11); *Y02P 20/152* (2015.11)

(56) References Cited

U.S. PATENT DOCUMENTS 9,840,514 B2 * 12/2017 Ma ........................ C07D 493/10
2010/0326273 A1 * 12/2010 Liu ..................... B01D 67/0079
95/45

2016/0102177 A1 * 4/2016 Ghanem ................ B01D 71/64
95/47

OTHER PUBLICATIONS

Ma, Xiaohua et al., "Synthesis and Gas Transport Properties of Hydroxyl-Functionalized Polyimides with Intrinsic Microporosity", Macromolecules, Apr. 2012, 45, pp. 3841-3849. (Year: 2012).*
International Search Report and Written Opinion of Application No. PCT/IB2015/001396 dated Jan. 25, 2016, 18 pages.
Xiaohua Ma et al: "Synthesis and Gas 1,2,8,9, Transport Properties of 15-19 Hydroxyl-Functionalized Polyimides with Intrinsic Microporosity", Macromolecules, vol. 45, No. 9, May 8, 2012 (May 8, 2012), pp. 3841-3849, XP055050229, ISSN: 0024-9297.
Xiaohua Ma et al: "Novel Spirobifluorene and Dibromospirobifluorene-Based Polyimides of Intrinsic Microporosity for Gas Separation Applications", Macromolecules, vol. 46, No. 24, Dec. 23, 2013 (Dec. 23, 2013), pp. 9618-9624, XP055220987, us ISSN: 0024-9297.
Chul Ho Jung and Young Moo Lee: "Gas permeation properties of hydroxyl-group containing polyimide membranes", Macromolecular Research, Polymer Society of Korea, Seoul, KR, vol. 16, No. 6, Jan. 1, 2008 (Jan. 1, 2008), pp. 555-560, XP008146669, ISSN: 1598-5032.

* cited by examiner

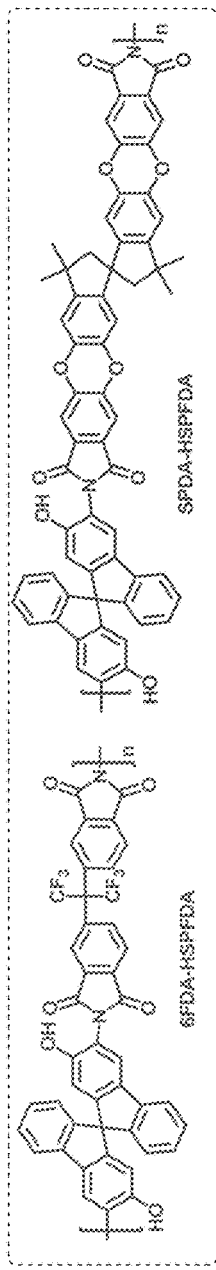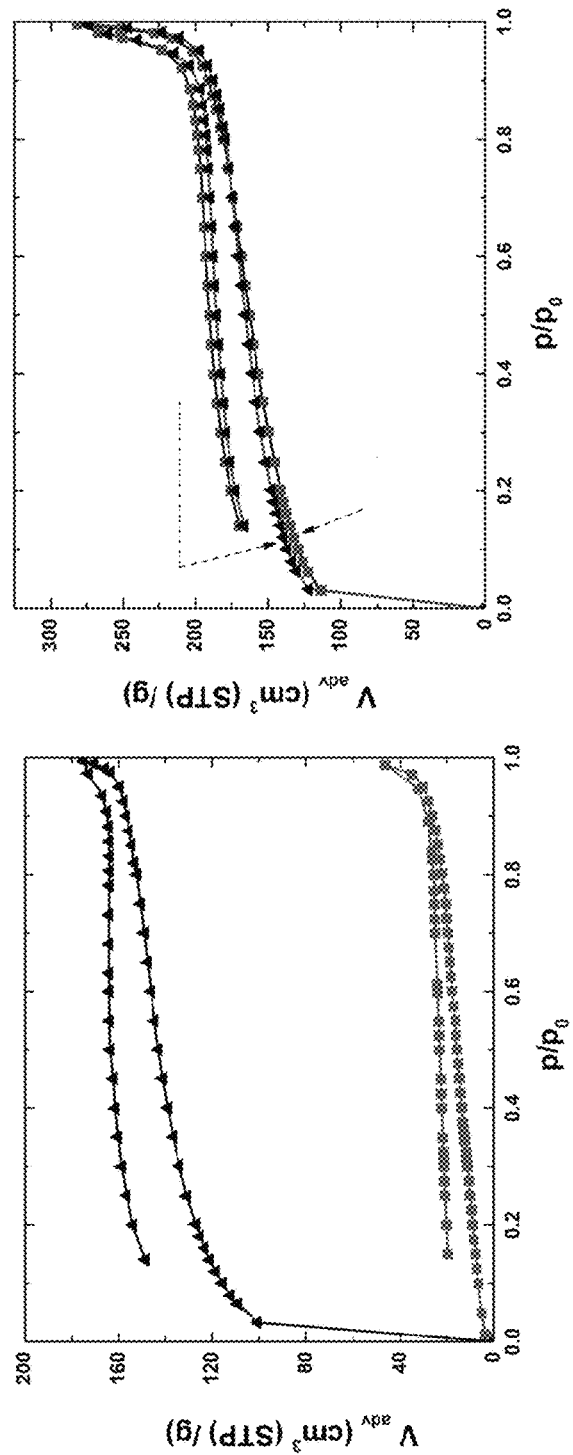
Fig. 4
$N_2$ adsorption/desorption isotherms of the polymers before and after TR

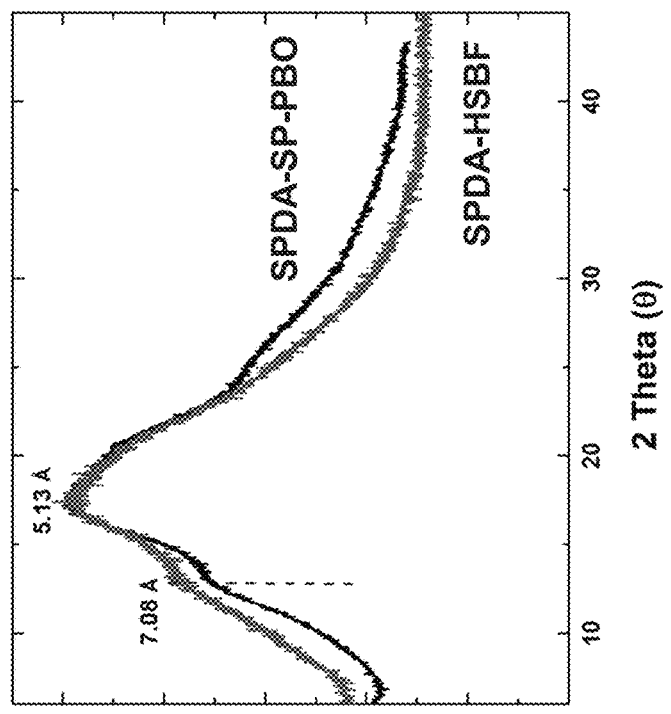
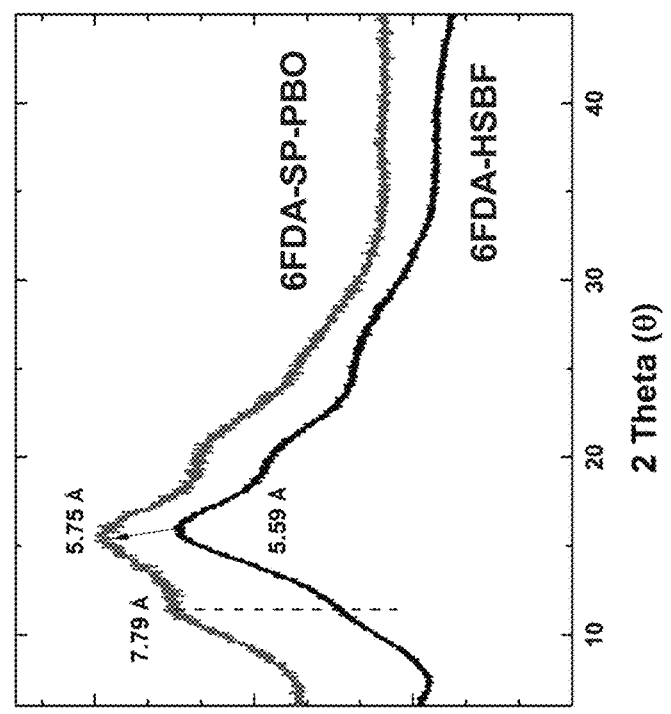
Fig. 5

Permeability and selectivity of the membranes for different gases at 35 °C

| Polymers | Permeability (Barrer)[a] | | | | | Ideal Selectivity (α) | | |
|---|---|---|---|---|---|---|---|---|
| | $H_2$ | $N_2$ | $O_2$ | $CH_4$ | $CO_2$ | $O_2/N_2$ | $CO_2/N_2$ | $CO_2/CH_4$ |
| 6FDA–SBF | 234 | 7.8 | 35.1 | 6.4 | 182 | 4.5 | 23.3 | 27.3 |
| 6FDA–HSBF | 162 | 3.8 | 19.3 | 2.4 | 100 | 5.1 | 26.3 | 41.7 |
| 6FDA–SP–PBO | 985 | 55 | 215 | 56 | 1,158 | 3.9 | 21.1 | 20.7 |
| SPDA–SBF | 501 | 28.6 | 111 | 41.1 | 614 | 3.9 | 21.5 | 14.9 |
| SPDA–HSBF | 519 | 24 | 98 | 29 | 568 | 4.1 | 23.7 | 19.6 |
| SPDA–SP–PBO | 775 | 61.6 | 225 | 84.8 | 1,279 | 3.7 | 20.8 | 15.1 |

Diffusion coefficient (D), solubility coefficient (S), diffusion selectivity ($\alpha_D$) and solubility selectivity ($\alpha_S$) for different gases of various membranes

| Polymers | $D^a$ | | $S^b$ | | $\alpha_D$ | $\alpha_S$ |
| --- | --- | --- | --- | --- | --- | --- |
| | $CH_4$ | $CO_2$ | $CH_4$ | $CO_2$ | $CO_2/CH_4$ | $CO_2/CH_4$ |
| 6FDA-SBF | 1.2 | 7.2 | 5.3 | 25 | 6.0 | 4.7 |
| 6FDA–HSBF | 0.46 | 3.71 | 5.17 | 26.8 | 8.1 | 5.2 |
| 6FDA-SP-PBO | 3.91 | 22.6 | 14.4 | 51.1 | 5.8 | 3.6 |

$^a$ D is determined by constant volume time-lag method, scale: $10^{-8}$ $cm^2/s$; $^b$ S is deduced based on the equation $P = D \times S$, scale: $10^{-2}$ $cm^3/cm^3$ cmHg

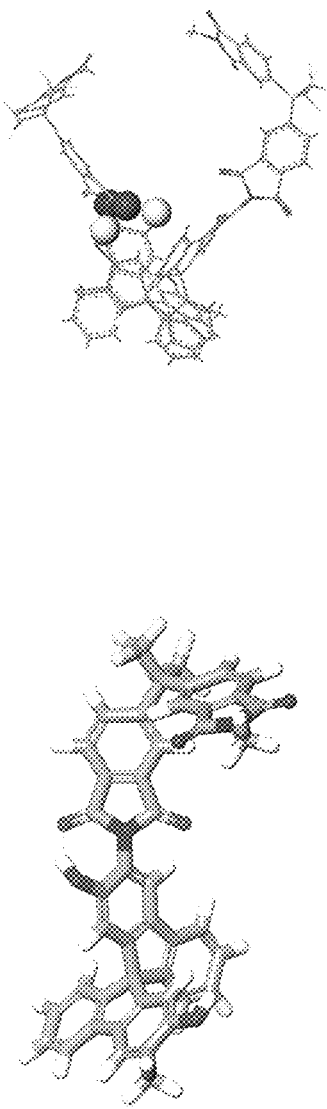

Fig. 8

$^1$H NMR of the monomer and polymers, DMSO-$d_6$ was used as solvent.

TGA curve of the pristine and thermal rearranged polymer membranes

O-HYDROXY-FUNCTIONALIZED DIAMINES, POLYIMIDES, METHODS OF MAKING EACH, AND METHODS OF USE

CROSS-REFERENCE TO RELATED APPLICATIONS

This application is the National Stage of International Application No. PCT/IB2015/001396, filed 14 Jul. 2015, which claims the benefit of and priority to U.S. Provisional Application Ser. No. 62/024,487, having the title "O-HYDROXY-FUNCTIONALIZED DIAMINES, POLYIMIDES, METHODS OF MAKING EACH, AND METHODS OF USE," filed on 15 Jul. 2014, the entire disclosures of which are incorporated by reference in their entireties as if fully set forth herein.

BACKGROUND

Polyimides are among the most important high-performance glassy polymers that exhibit exceptional thermal, chemical, and mechanical properties. Polyimides have been used in many areas including the aerospace industry, electronic industry, high temperature adhesion, membranes for separation, composite materials, and the like. However, most polyimides exhibit poor processability due to their high melting points and limited solubility in organic solvents. Microporous polyimides have been developed to overcome these deficiencies, however, microporous polyimides are challenging to synthesize due, at least in part, to limitations of suitable reagents.

SUMMARY

Embodiments of the present disclosure provide for aromatic ortho-hydroxy-functionalized diamines, a method of making aromatic ortho-hydroxy-functionalized diamines, aromatic ortho-hydroxy-functionalized diamines-based polyimides, a method of making aromatic ortho-hydroxy-functionalized diamines-based polyimides, methods for gas separations and the like.

An embodiment of the present disclosure provides for a composition, among others, that includes: an o-hydroxy-functionalized diamine having the following structure:

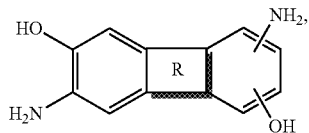

wherein R is selected from the following structures:

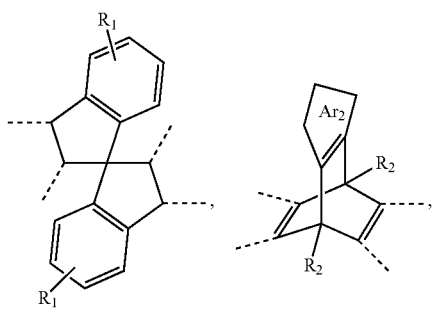

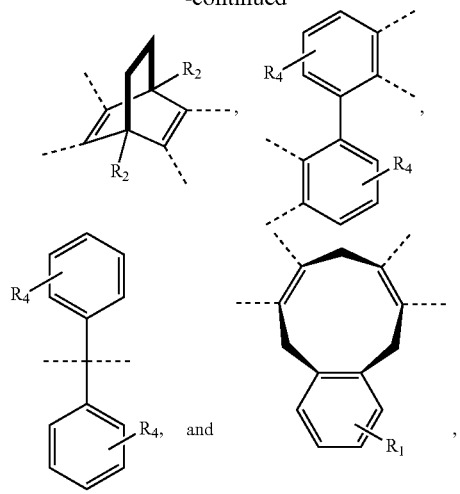

wherein each $R_1$, $R_2$, and $R_4$ are independently selected from the group consisting of: a linear or branched, substituted or unsubstituted, alkyl group, wherein $Ar_2$ is selected from the group consisting of: an aryl group and a heteroaryl group where each are substituted or unsubstituted.

An embodiment of the present disclosure provides for a composition, among others, that includes: a polyimide having the following structure:

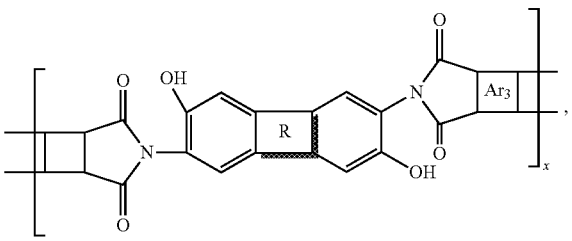

wherein $Ar_3$ is selected from an aryl group or a heteroaryl group, wherein x is 1 to 100,000, wherein R is selected from the following structures:

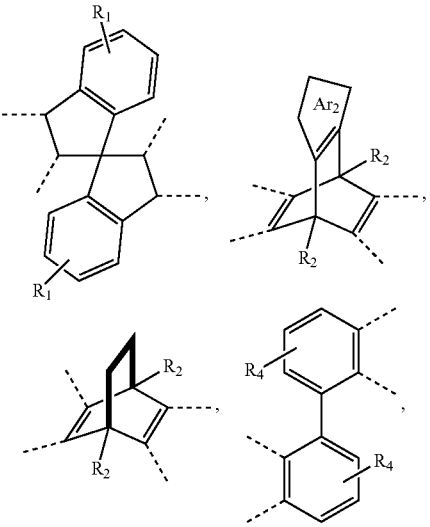

-continued

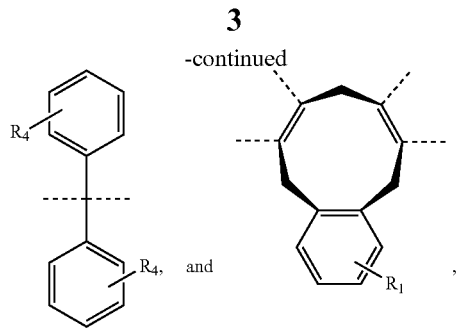

wherein each of $R_1$, $R_2$, and $R_4$ are independently selected from the group consisting of: a linear or branched, substituted or unsubstituted alkyl group, wherein $Ar_2$ is selected from the group consisting of: an aryl group and a heteroaryl group where each can be substituted or unsubstituted.

An embodiment of the present disclosure provides for a method of making an aromatic diamine, among others, that includes:

-continued

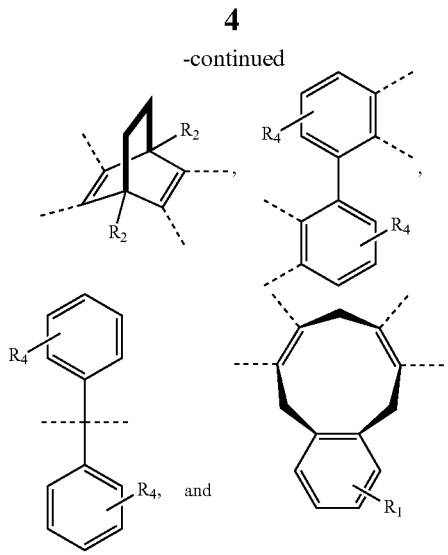

wherein $R_1$, $R_2$, and $R_4$ are independently selected from the group consisting of: a linear or branched, substituted or unsubstituted alkyl group, wherein $Ar_2$ is selected from the

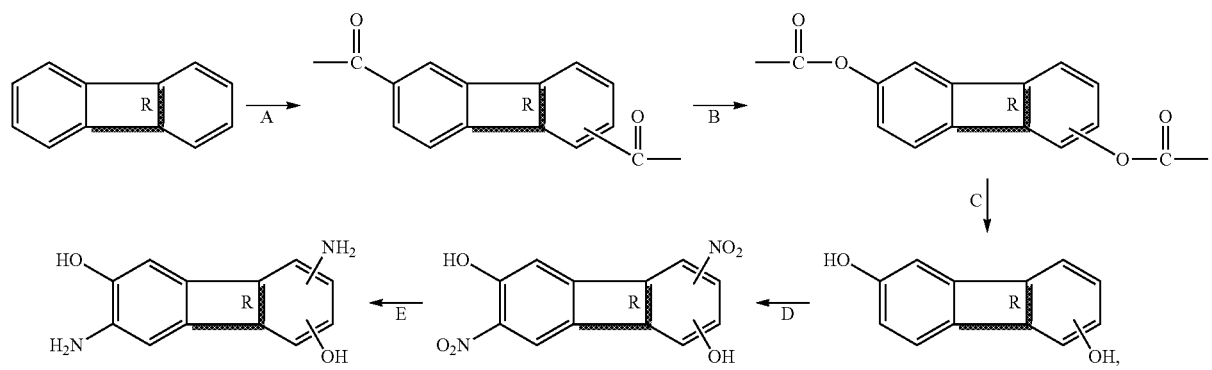

wherein A includes acetylation of the bulky starting structures by Friedel-Crafts reaction, wherein B includes transferring the diacetyl intermediate to diester via Baeyer-Villiger oxidation reaction, wherein C includes the hydrolysis of the diester, wherein D includes the nitration of the diphenol intermediate, wherein E includes the reduction of the ortho-diphenol-dinitrol intermediate to the corresponding ortho-hydroxy-functionalized diamine, wherein R is selected from the following structures:

group consisting of: an aryl group and a heteroaryl group where each is substituted or unsubstituted.

An embodiment of the present disclosure provides for a method of making a polyimide, among others, that includes: reacting a dianhydride with an o-hydroxy-functionalized diamine to form a polyimide, wherein the o-hydroxy-functionalized diamine has the following structure:

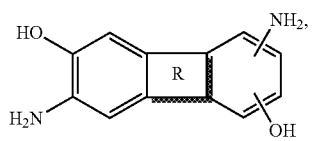

wherein R is selected from the following structures:

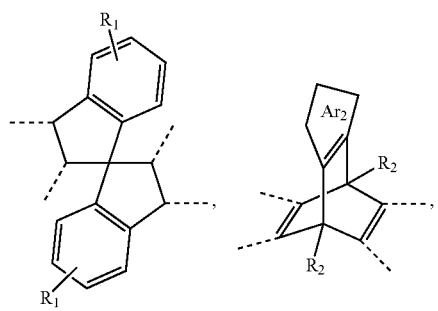

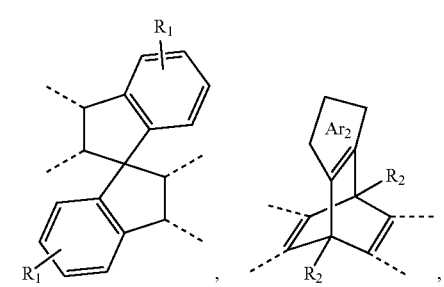

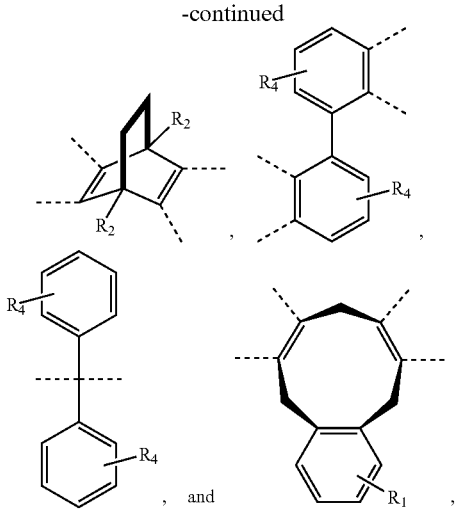

, and 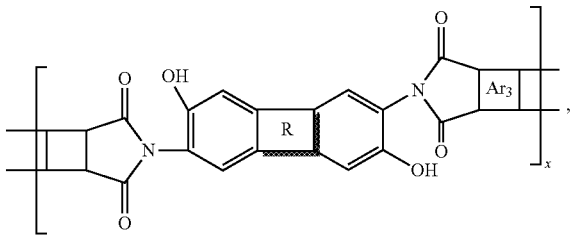, wherein each $R_1$, $R_2$, and $R_4$ are independently selected from the group consisting of: a linear or branched, substituted or unsubstituted, alkyl group, wherein $Ar_2$ is selected from the group consisting of: an aryl group and a heteroaryl group where each are substituted or unsubstituted.

An embodiment of the present disclosure provides for a membrane, among others, that includes: a polyimide having the following structure:

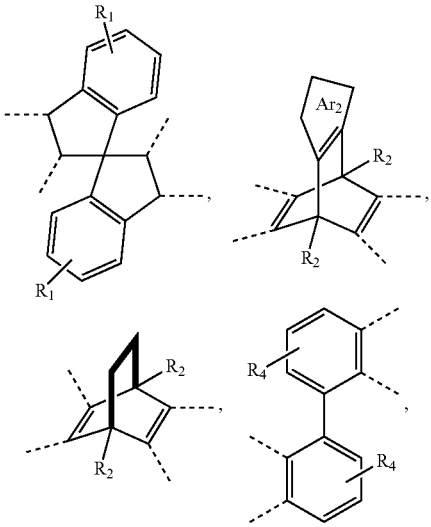

wherein $Ar_3$ is selected from an aryl group or a heteroaryl group, wherein x is 1 to 100,000, wherein R is selected from the following structures:

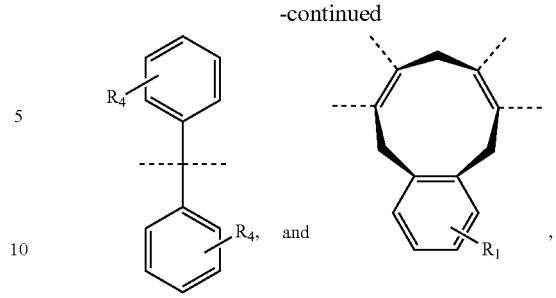

wherein each of $R_1$, $R_2$, and $R_4$ are independently selected from the group consisting of: a linear or branched, substituted or unsubstituted alkyl group, wherein $Ar_2$ is selected from the group consisting of: an aryl group and a heteroaryl group where each can be substituted or unsubstituted.

An embodiment of the present disclosure provides for a method of separating a gas from a gas mixture, among others, that includes: separating a first gas from a first gas mixture containing at least a second gas with a membrane to form a second gas mixture that is enriched in at least one gas component of the first mixture, wherein the membrane includes a polyimide having the following structure:

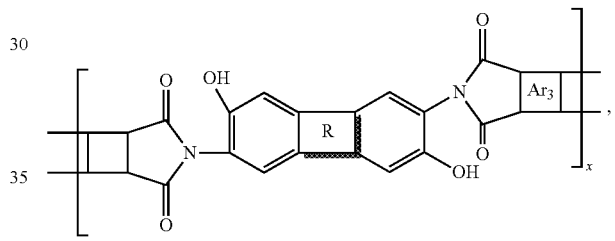

wherein $Ar_3$ is selected from an aryl group or a heteroaryl group, wherein x is 1 to 100,000, wherein R is selected from the following structures:

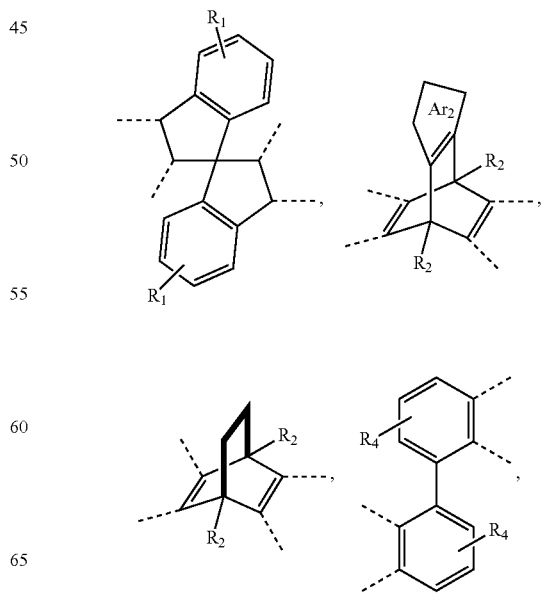

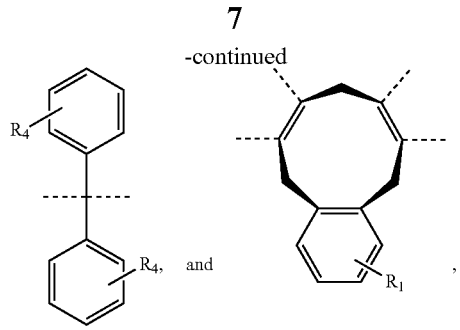

wherein each of $R_1$, $R_2$, and $R_4$ are independently selected from the group consisting of: a linear or branched, substituted or unsubstituted alkyl group, wherein $Ar_2$ is selected from the group consisting of: an aryl group and a heteroaryl group where each can be substituted or unsubstituted.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 4 illustrates the $N_2$ Adsorption/Desorption isotherms of 6FDA-HSBF ($S_{BET}$=70 m²/g) (■) and 6FDA-SP-PBO ($S_{BET}$=420 m²/g) (▲) (left) and SPDA-HSBF ($S_{BET}$=460 m²/g) (■) and SPDA-SP-PBO ($S_{BET}$=480 m²/g) (▲)(right) (i.e., before and after TR), according to one or more embodiments of the present disclosure.

FIG. 5 illustrates the Wide-Angle X-Ray Diffraction (WAXD) of 6FDA-HSBF and 6FDA-SP-PBO (left) and SPDA-HSBF and SPDA-SP-PBO (right), according to one or more embodiments of the present disclosure.

FIG. 8 tabulates the diffusion and Solubility coefficients of permeation properties for 6FDA-SBF, 6FDA-HSBF, and 6FDA-SP-PBO, according to one or more embodiments of the present disclosure.

DETAILED DESCRIPTION

Figure 1:
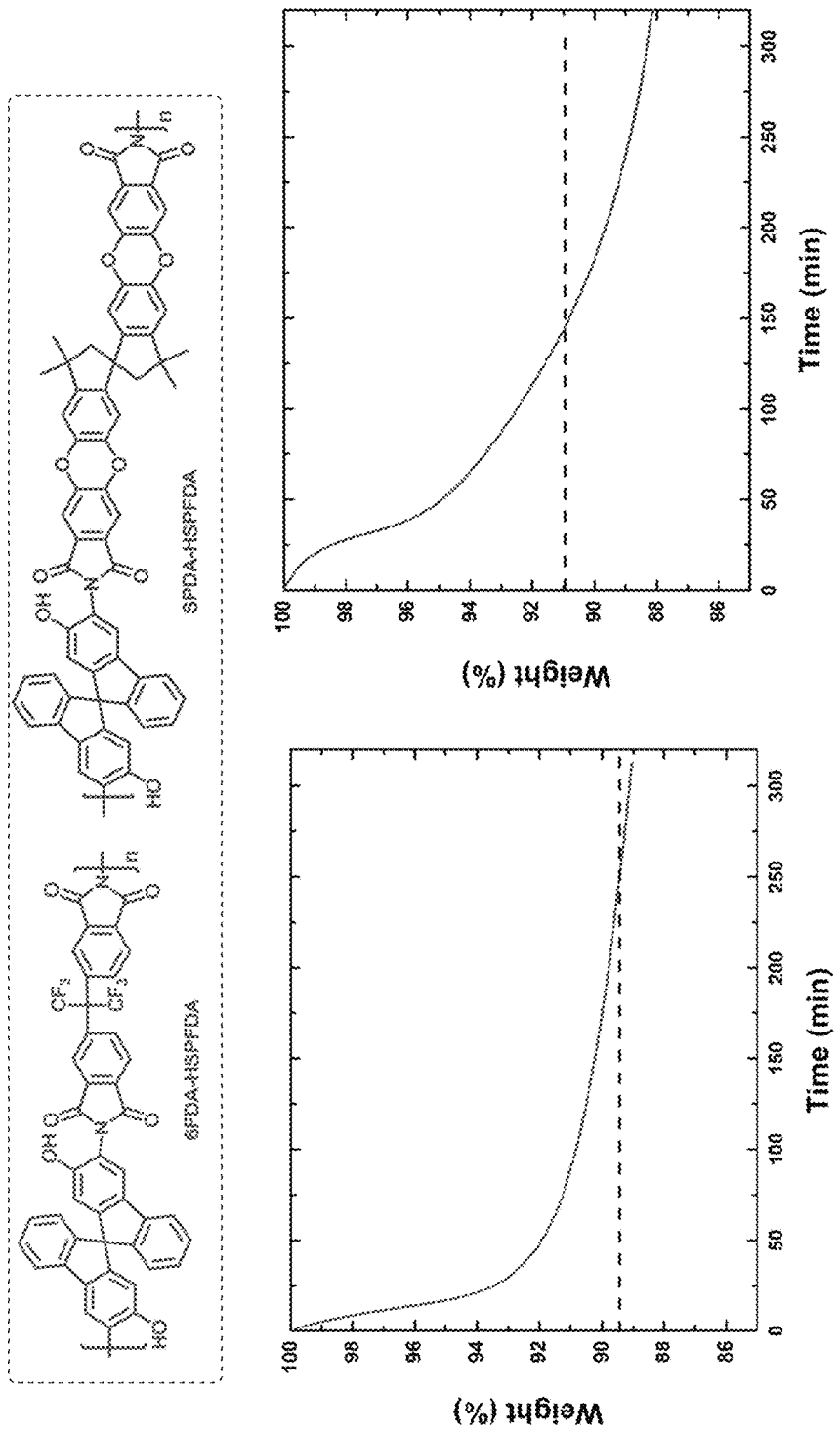
FIG. 1 illustrates the conditions for polybenzoxazole (PBO) formation 6FDA-HSBF (left) and SPDA-HSBF (right) by thermal rearrangement (TR) (420° C. for 4 hrs and 450° C. for 2 hrs, respectively), according to one or more embodiments of the present disclosure.
Figure 2:
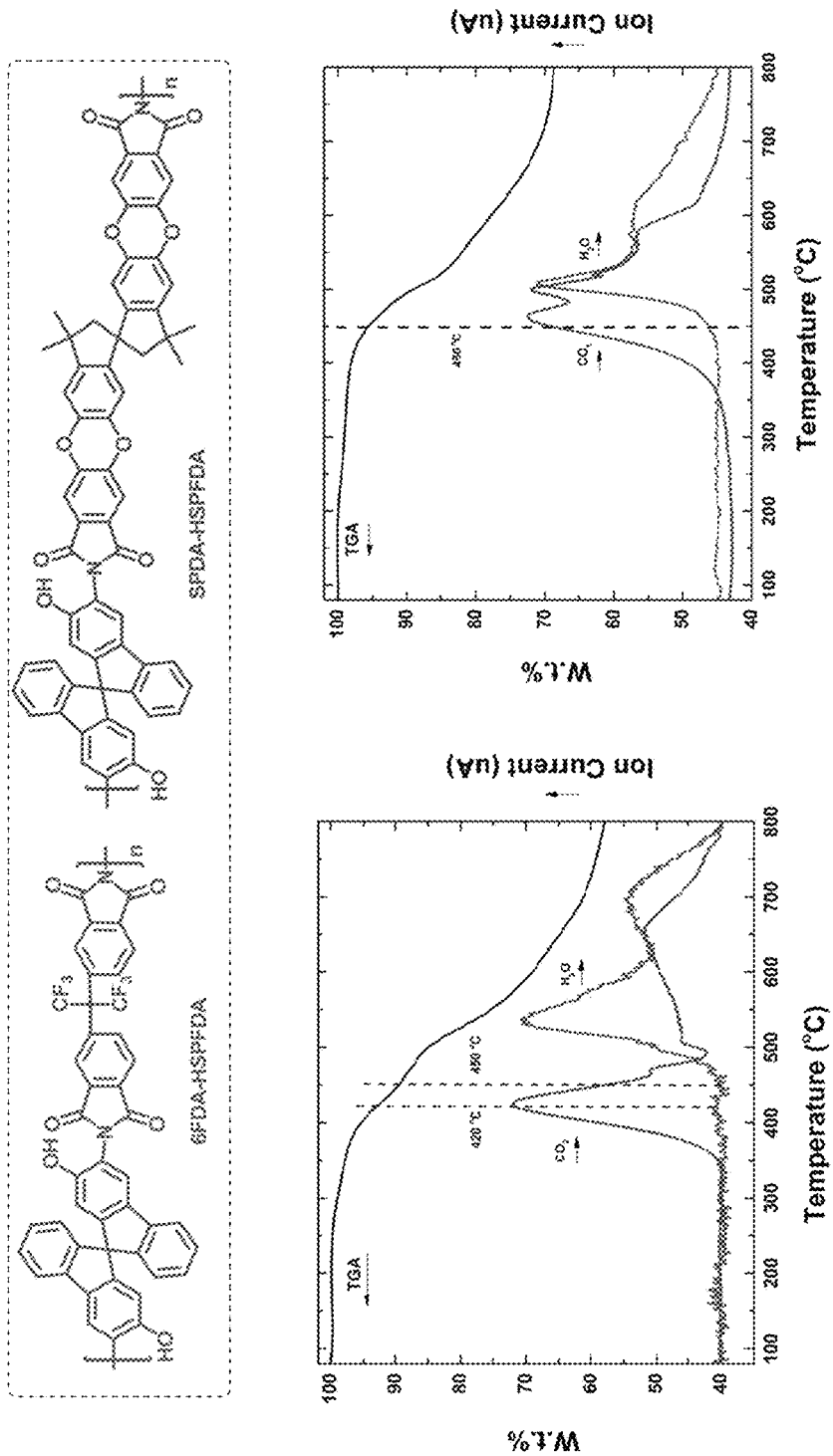
FIG. 2 illustrates the thermal properties of 6FDA-HSBF (left) and SPDA-HSBF (right) as determined by Thermogravimetric Analysis (TGA) with a Quadrupole Mass Spectrometeter (QMS), according to one or more embodiments of the present disclosure.
Figure 3:
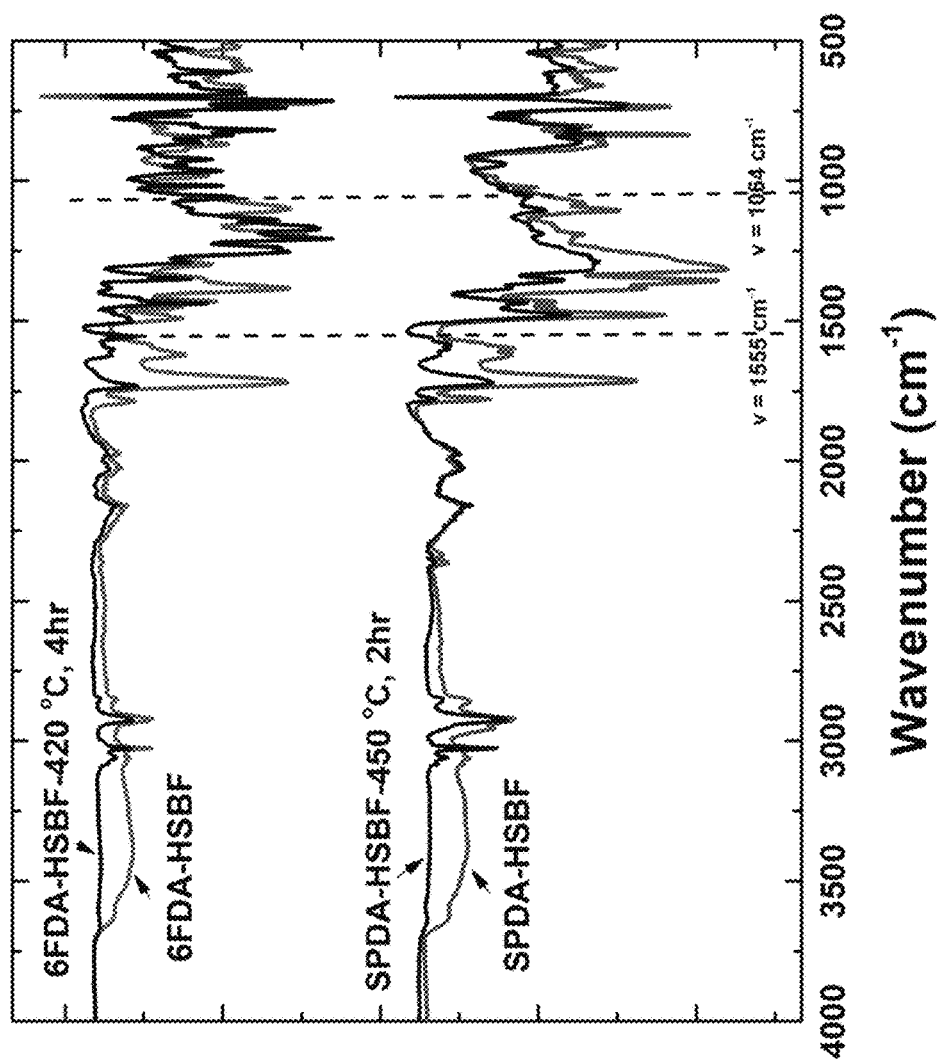
FIG. 3 illustrates the Fourier Transform Infrared (FT-IR) Spectra for 6FDA-HSBF (upper) and SPDA-HSBF (lower), before and after TR, according to Example 1.
Figure 6:
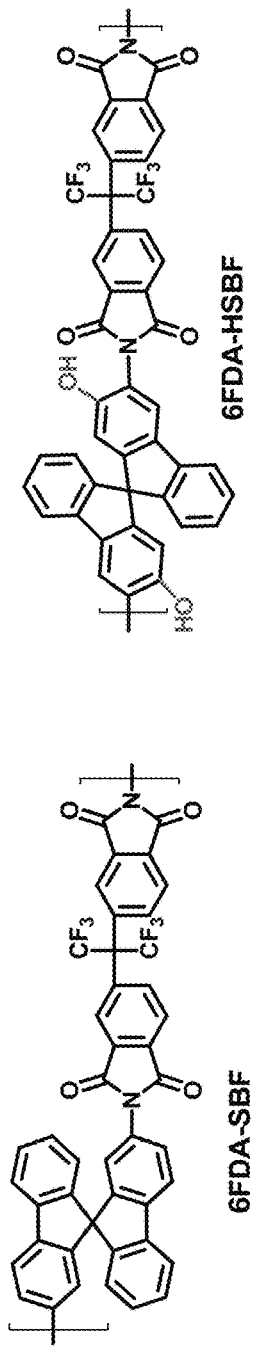
FIG. 6 tabulates the gas permeation properties (Barrer and α) of films obtained from 6FDA-SBF, 6FDA-HSBF, 6FDA-SP-PBO, SPDA-SPF, SPDA-HSBF and SPDA-SP-PBO for each of $H_2$, $N_2$, $O_2$, $CH_4$, $CO_2$, $O_2/N_2$, $CO_2/N_2$, and $CO_2/CH_4$ at 35° C., according to one or more embodiments of the present disclosure.
Figure 7:
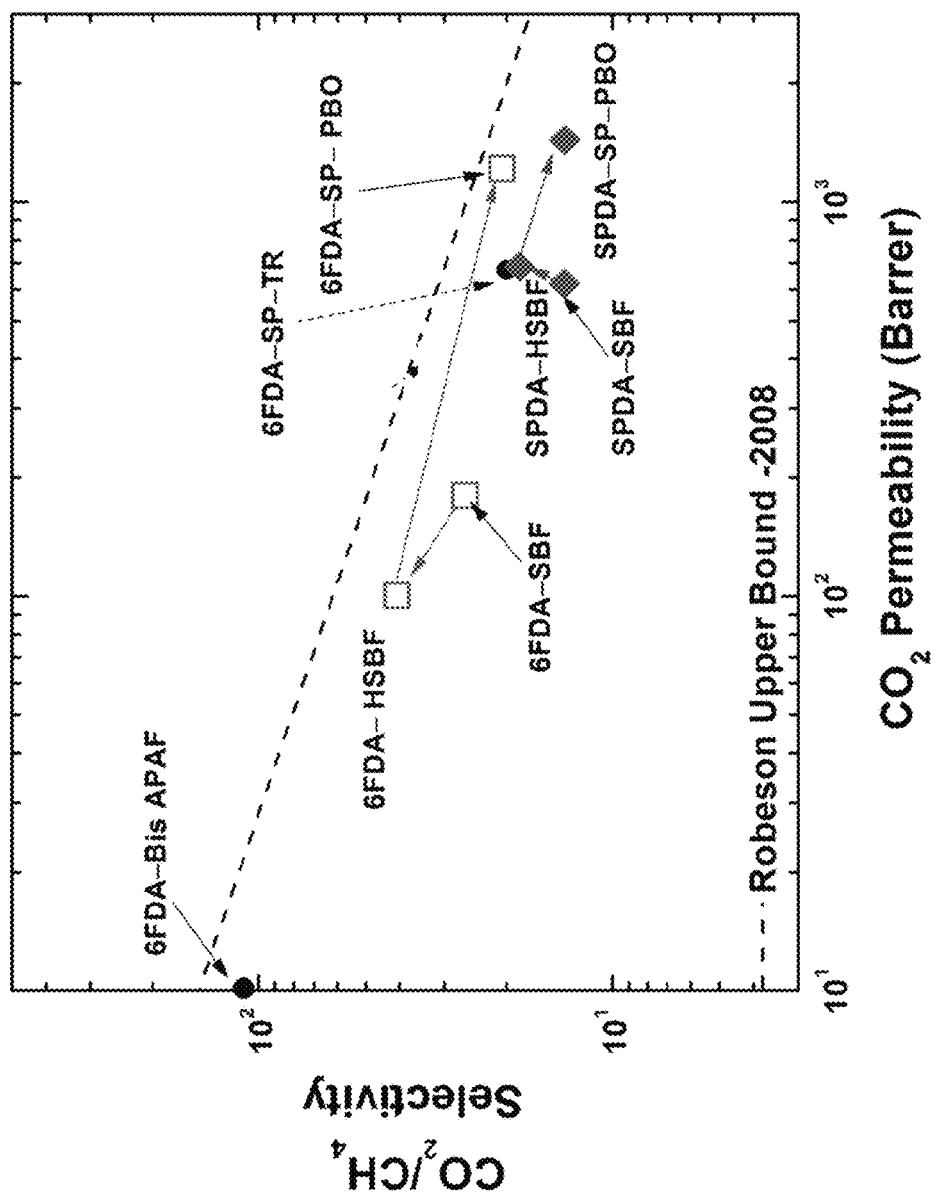
FIG. 7 illustrates the Permeability/Selectivity Map ($CO_2$ permeability (Barrer) v. $CO_2/CH_4$ Selectivity (α)) for films obtained from 6FDA-SBF, 6FDA-HSBF, 6FDA-SP-PBO, SPDA-SPF, SPDA-HSBF, SPDA-SP-PBO, 6FDA-SP-TR and 6FDA-Bis APAF, according to one or more embodiments of the present disclosure.
Figure 9:
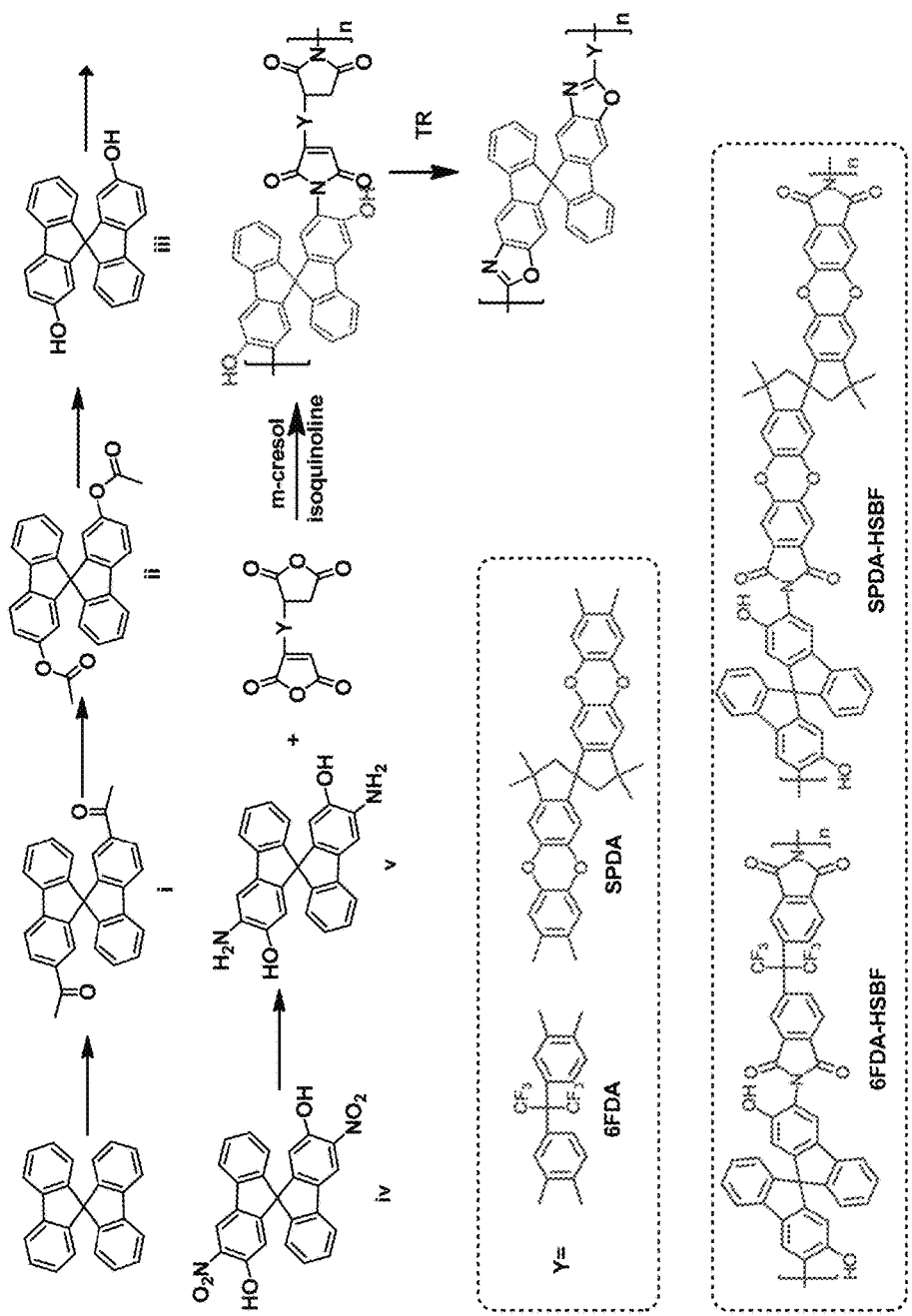
FIG. 9 illustrates the scheme for synthesis of 6FDA-HSBF and SPDA-HSBF, according to Example 1.
Figure 10:
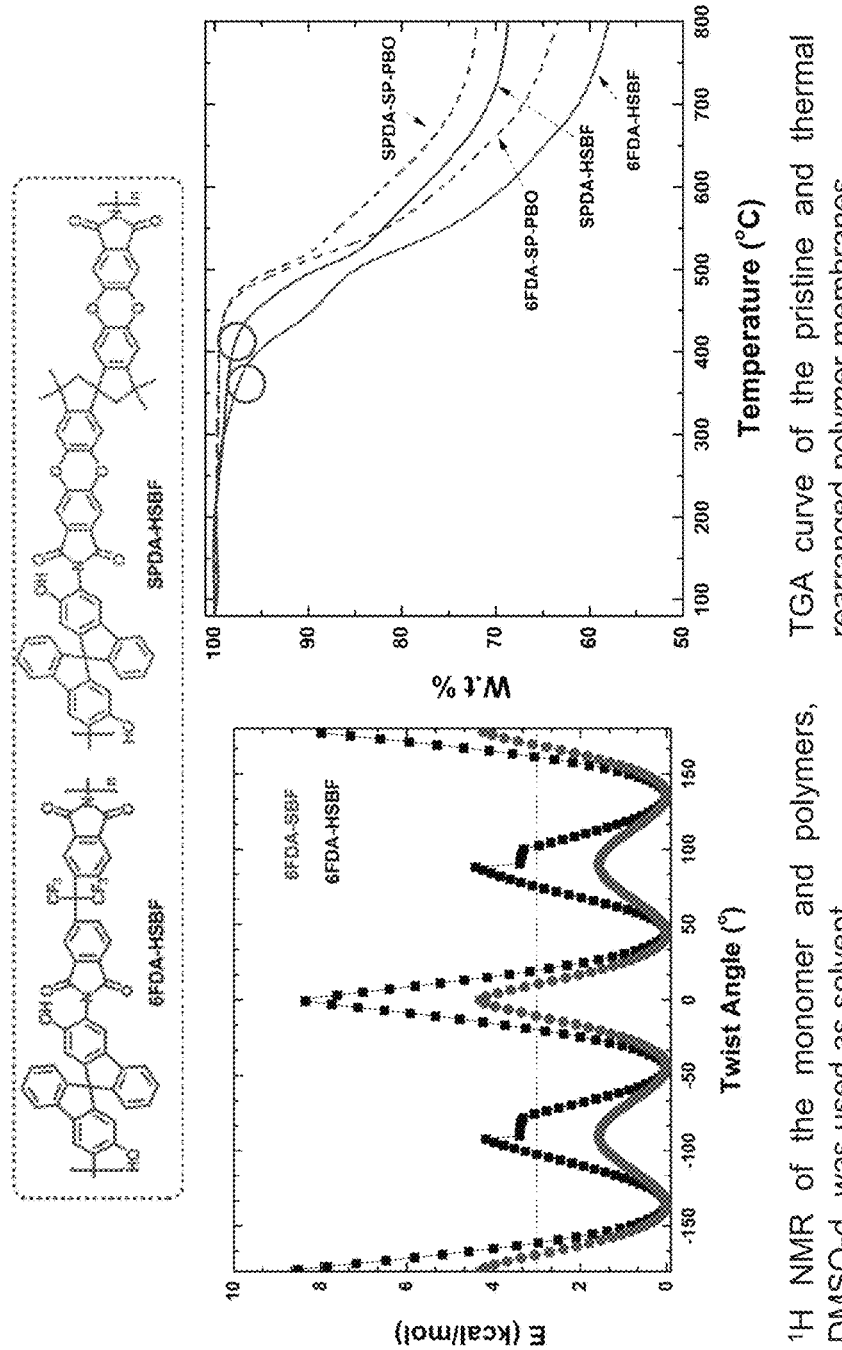
FIG. 10 illustrates the 1H NMR spectra of 6FDA-HSBF and 6FDA-SBF (monomer and polymer) (left) and a TGA curve of pristine and TR polymer membranes of 6FDA-HSBF, 6FDA-SP-PBO, SPDA-HSBF, and SPDA-SP-PBO (right), according to one or more embodiments of the present disclosure.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, synthetic organic chemistry, polymer chemistry, analytical chemistry, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in bar. Standard temperature and pressure are defined as 0° C. and 1 bar.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions

The term "substituted" refers to any one or more hydrogens on the designated atom that can be replaced with a selection from the indicated group, provided that the designated atom's normal valence is not exceeded.

As used herein, "aliphatic" or "aliphatic group" refers to a saturated or unsaturated, linear or branched, cyclic (non-aromatic) or heterocyclic (non-aromatic), hydrocarbon or hydrocarbon group and encompasses alkyl, alkenyl, and alkynyl groups, and alkanes, alkene, and alkynes, for example.

As used herein, "cyclic" group refers to a cyclic hydrocarbon having a stable 4, 5, 6, 7, 8, 9, 10, 11, or 12 membered (e.g., carbon or hetero), (unless the number of members is otherwise recited), monocyclic, bicyclic, or tricyclic cyclic ring.

As used herein, "alkyl" or "alkyl group" refers to a branched saturated aliphatic hydrocarbon. Examples of alkyl include, but are not limited to iso-propyl, sec-butyl, t-butyl, and iso-pentyl.

The term "substituted," as in "substituted alkyl", "substituted aryl," "substituted heteroaryl" and the like means that the substituted group may contain in place of one or more hydrogens a group such as alkyl, hydroxy, amino, halo, trifluoromethyl, cyano, —NH(lower alkyl), —N(lower alkyl)$_2$, lower alkoxy, lower alkylthio, or carboxy, and thus embraces the terms haloalkyl, alkoxy, fluorobenzyl, and the sulfur and phosphorous containing substitutions referred to below.

As used herein, "halo", "halogen", or "halogen radical" refers to fluorine, chlorine, bromine, and iodine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

The term "aryl" as used herein, refers to an aromatic monocyclic or multicyclic ring system of about 6 to about 14 carbon atoms, preferably of about 6 to about 10 carbon atoms. Exemplary aryl groups include phenyl or naphthyl, or phenyl substituted or naphthyl substituted.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures. Preferred examples are furanyl, imidazyl, pyranyl, pyrrolyl, and pyridyl.

General Discussion

Embodiments of the present disclosure provide for an ortho (o)-hydroxy-functionalized diamine, a method of making an o-hydroxy-functionalized diamine, an o-hydroxy-functionalized diamine-based polyimide, a method of making an o-hydroxy-functionalized diamine imide, methods of gas separation, and the like. Embodiments of the o-hydroxy-functionalized diamine can be used in the production of high-performance polymers such as polyimides, polypyrrolones, polyamides, polybenzoxazoles, and the like.

Embodiments of the present disclosure can be used or can be implemented in a wide range of industrial applications related to aerospace industry, electronic industry, optical industry, high temperature adhesion, membranes for separation, and composite materials. In particular, these materials can be used as thermally stable coatings, low dielectric constant films, optoelectronic materials, sensors, and gas storage media.

Embodiments of the o-hydroxy-functionalized diamine monomers and o-hydroxy-functionalized diamine-based aromatic polyimides are expected to be economically attractive compared with the current polymer-based membranes due to their high permeabilities and excellent selectivities. Higher permeability offers savings in capital cost of membrane systems by reducing area requirements to handle a given process flow. It also reduces energy consumption by reducing compression requirements. Higher selectivity introduces large savings by reducing cross-over of valuable gas feed components into the permeate streams and also by reducing the need for multi-stage systems.

In an exemplary embodiment, an o-hydroxy-functionalized diamine-based aromatic polyimide can be used to form a gas separation membrane. The membrane can have exceptional performance for gas separation applications. Specifically, embodiments of membranes incorporating the o-hydroxy-functionalized diamine-based polyimide provide excellent performance in gas separation applications including nitrogen enrichment and hydrogen recovery from ammonia purge-gas streams. In addition, embodiments of membranes incorporating the o-hydroxy-functionalized diamine-based polyimide have excellent performance in olefin/paraffin ($C_3H_6/C_3H_8$) and natural gas sweetening ($CO_2/CH_4$) applications. In particular, exemplary embodiments of the o-hydroxy-functionalized diamine-based aromatic polyimides when used in gas separation membranes demonstrate permeability and selectivity in air separations (i.e., $O_2/N_2$ in nitrogen enrichment), hydrogen separations (i.e., $H_2/N_2$ and $H_2/CH_4$ for hydrogen recovery from ammonia purge gas streams), and challenging olefin/paraffin separations (i.e., $C_3H_6/C_3H_8$).

In an exemplary embodiment, the o-hydroxy-functionalized diamine-based polyimide can be made using an o-hydroxy-functionalized diamine as shown in the following structure:

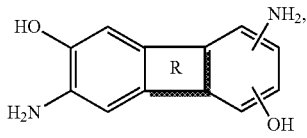

In an embodiment, the o-hydroxy-functionalized diamine can have the following structure:

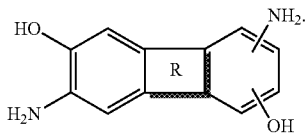

In an embodiment, R can be selected from the following structures, where each structure can be substituted or unsubstituted, and bonded via the bonds noted by hash marks:

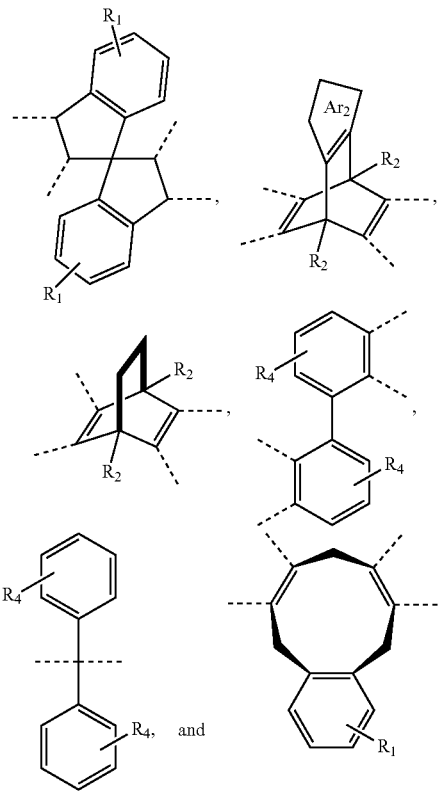

In an embodiment, each $R_1$, $R_2$, and $R_4$ can be independently selected from: H or a linear or branched, substituted or unsubstituted alkyl group. In an embodiment, each $R_1$, $R_2$, and $R_4$ can be independently selected from a methyl group, an ethyl group, a propyl group, and a butyl group (linear or branched), each substituted or unsubstituted. The phrase "independently selected from" can mean selection from $R_1$, $R_2$, and $R_4$ independent of one another, or can mean that in each instance of $R_1$ (as well as $R_2$ and $R_4$), each $R_1$ is selected independently of the other $R_1$s (e.g., one $R_1$ can be a methyl group and the other $R_1$ can be a propyl group).

Embodiments where $R_1$ is indicated as attached to a ring (e.g., an aromatic ring), $R_1$ can be attached to any carbon of the ring. Embodiments where $R_1$ is attached to a ring, one, two, or more $R_1$s can be attached to the ring to replace hydrogens on the ring (use of only a singe $R_1$ group in the structures was done for reasons of clarity). For example, the ring can have two or more $R_1$s (e.g., up to 4 $R_1$s) attached to the same ring at the same or different carbons.

In an embodiment, $Ar_2$ can be an aryl group or a heteroaryl group, where $Ar_2$ can be substituted or unsubstituted. In an embodiment, $Ar_2$ can be selected from:

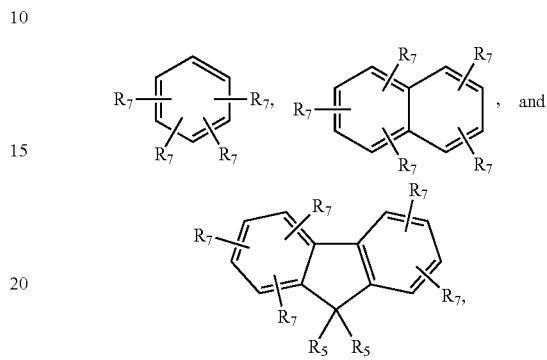

that is bonded by removing a hydrogen from the ring for two carbons and each ring can have up to four $R_7$ groups. In an embodiment, $Ar_2$ can be selected from

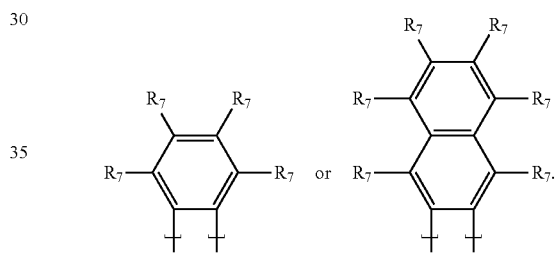

In an embodiment, each $R_5$ and $R_7$ can be independently selected from H or a linear or branched, substituted or unsubstituted, alkyl group (e.g., methyl group). Each $R_5$ can be independently selected. Each $R_7$ can be independently selected.

In an embodiment, the o-hydroxy-functionalized diamine can be produced using the reaction sequence shown below, while specific embodiments of methods of synthesis are described in the examples.

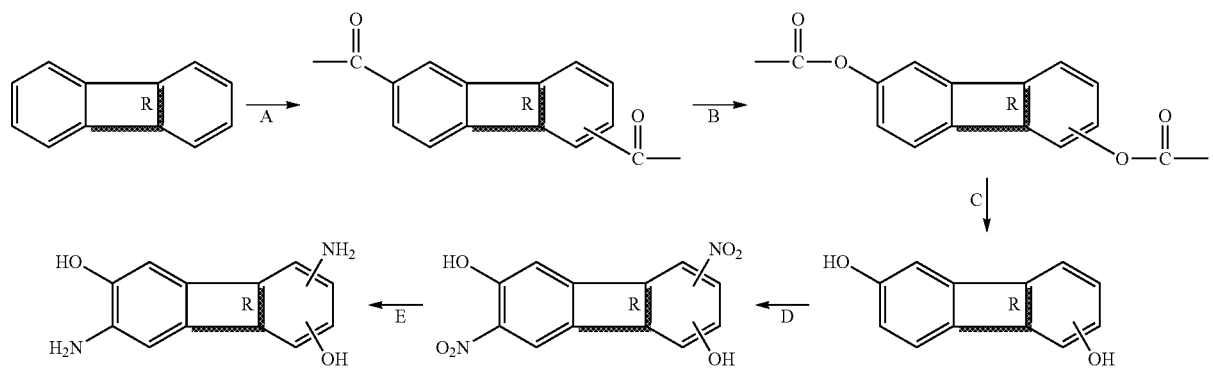

R and the other variables are defined as noted above. In an embodiment, step A includes the acetylation of the bulky starting structures by Friedal-Crafts reaction under a catalyst such as aluminum trichloride. The reaction can take place at a temperature of about −10° C. to room temperature over a time frame of about 10 hrs to 48 hrs.

In an embodiment, step B includes transferring the diacetyl intermediate to diester via Baeyer-Villiger oxidation reaction under the presence of a peroxide such as meta-chloroperoxybenzoic acid (m-CPBA). The reaction can take place at a temperature of about 40° C. to 70° C. over a time frame of about 24 to 48 hrs.

In an embodiment, step C includes the hydrolysis of the diester to obtain the diphenol intermediate. The reaction can take place at a temperature of about 0° C. to 30° C. over a time frame of about 1 hrs to 3 hrs.

In an embodiment, step D includes the nitration of the diphenol intermediate. The reaction can take place at a temperature of about 0° C. to 30° C. over a time frame of about 12 hrs to 24 hrs.

In an embodiment, step E includes the reduction of the ortho-diphenol-dinitrol intermediate to the corresponding ortho-hydroxy-functionalized diamine via Pd/C catalyst reduction reaction. The reaction can take place at a temperature of about 50° C. to 80° C. over a time frame of about 2 hrs to 4 hrs.

In an embodiment, the o-hydroxy-functionalized diamine can be used to form o-hydroxy-functionalized diamine-based polyimide homopolymers or co-polymers. In an embodiment, the o-hydroxy-functionalized diamine-based polyimide can have the following structure:

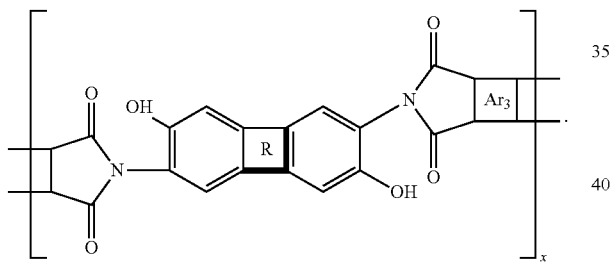

In an embodiment, Ar$_3$ can be an aryl group or heteroaryl group and x can be 1 to 10,000 or 1 to 100,000 or higher depending on the size of the polymer. In an embodiment, Ar$_3$ can be:

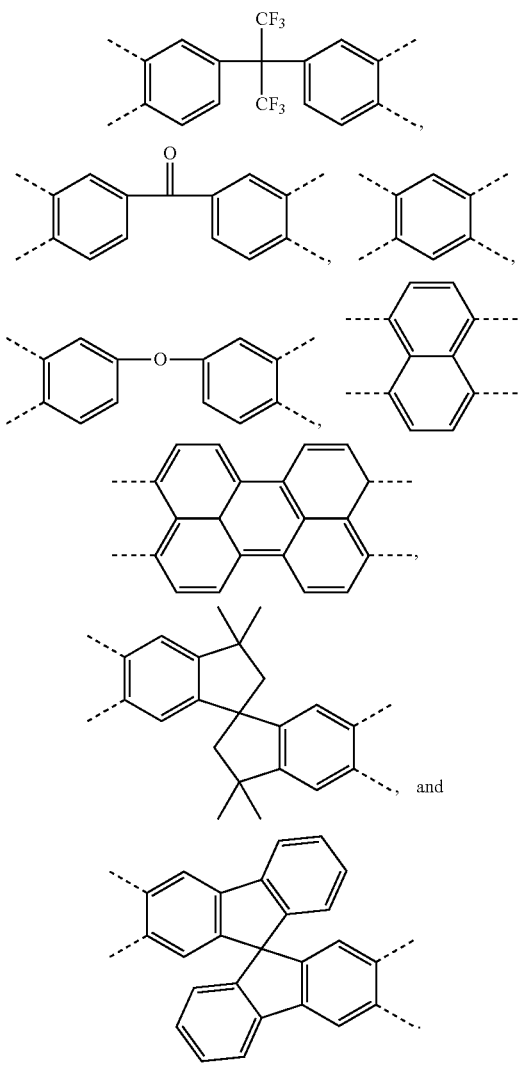

In an embodiment, the polymer can include two different Ar$_3$ groups to form a copolymer. For example, a copolymer can be formed according the scheme shown below where Ar$_3$ and Ar$_4$ are different (Ar$_4$ can be an aryl group or heteroaryl group, substituted or unsubstituted):

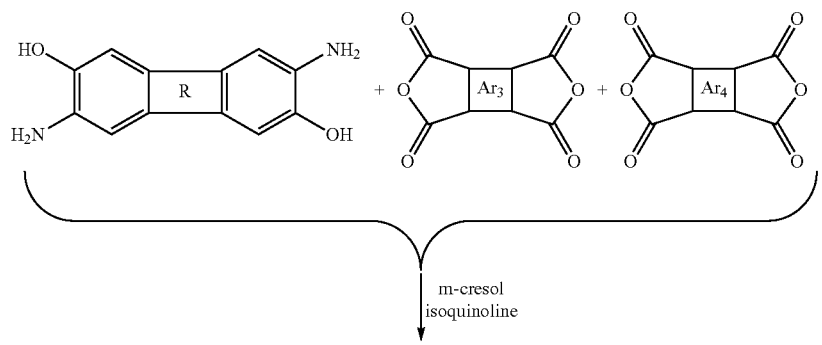

-continued

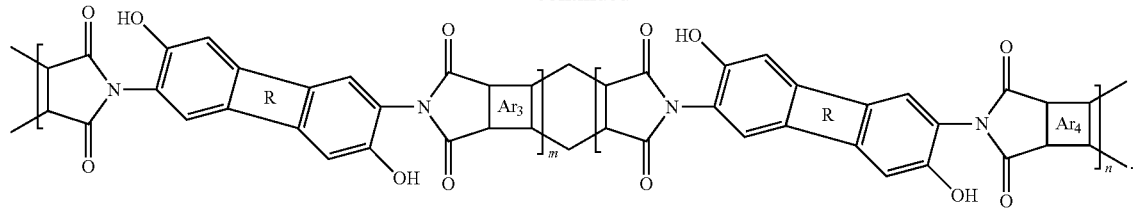

In another embodiment, hydroxy-functionalized multiamines can be formed and used to form hydroxy-functionalized multiamine-based polyimide. For example, the hydroxy-functionalized multiamine can be represented as:

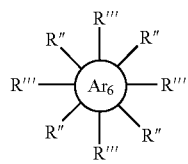

R'" can be OH and R" can be NH$_2$, where more or less R'" and R" groups can be present on the multiamine (but includes at least 2 of each). In an embodiment, the hydroxy-functionalized multiamines can be a diamine, triamine, tetramine, or an amine having 5 or more amino groups and multiple OH groups.

In an embodiment, the hydroxy-functionalized multiamine can have one of the following structures:

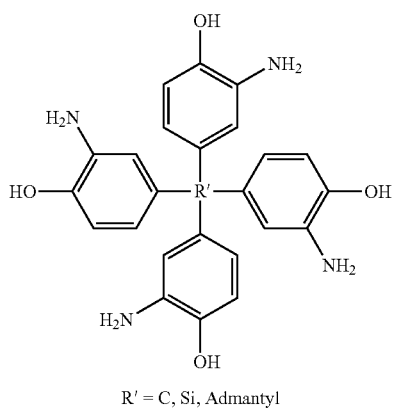

R' = C, Si, Admantyl

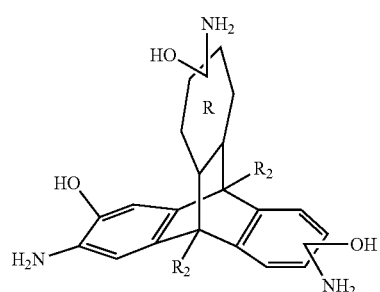

R$_2$ = H, Me, Et, isopropyl, etc

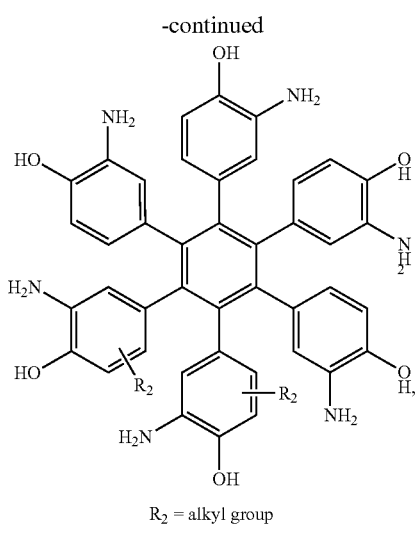

R$_2$ = alkyl group where R' can be C, S, or admantyl, R$_2$ can be H or alkyl (branded or linear).

In an embodiment, the hydroxy-functionalized multiamine can be formed according to the following reaction:

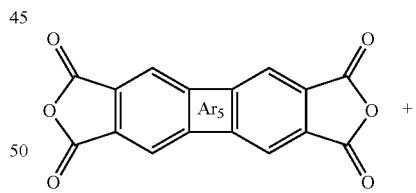

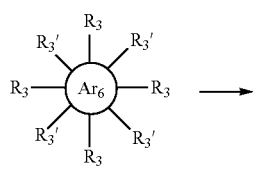

R$_3$, R$_3$' = OH, or NH$_2$

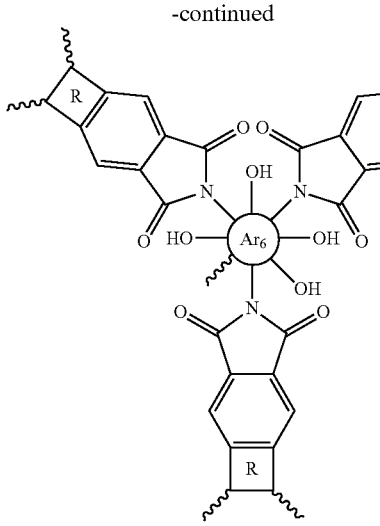

where Ar₅ and Ar₆ can be an aromatic group (e.g., aryl or heteroaryl, substituted or unsubstituted).

As mentioned above, polyimides of the present disclosure can be used to form membranes that can be used in gas separation. The membranes including the polyimides can be formed using conventional techniques, such as phase inversion, solution coating and the like.

As mentioned above, the membranes of the present disclosure can be used in conventional gas separation systems such as systems to enrich a specific gas content in a gas mixture (e.g., oxygen enrichment, nitrogen enrichment, and the like). In addition, the membranes can be used in hydrogen recovery applications and carbon dioxide removal gas separations.

In general, a first gas is separated from a first gas mixture (e.g., which can contain a second gas) with a membrane of the present disclosure to form a second gas mixture that is enriched in one or more components of the first gas mixture. In an embodiment, the result can be the separation of a gas(es) from another gas(es) such as in oxygen/nitrogen, hydrogen/methane, hydrogen/nitrogen, carbon dioxide/methane, carbon dioxide/nitrogen, hydrogen/$C_{2+}$ hydrocarbons, hydrogen sulfide/methane, carbon dioxide/hydrogen sulfide, ethylene/ethane, propylene/propane, water vapor/hydrocarbons, $C_{2+}$/hydrogen, $C_{2+}$/methane etc.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1: Synthesis of the Spirobifluorene-Based Monomer

Scheme S1: Synthesis of 3,3'-Diamino-2,2'-dihydroxy-9,9'-spirobifluorene.

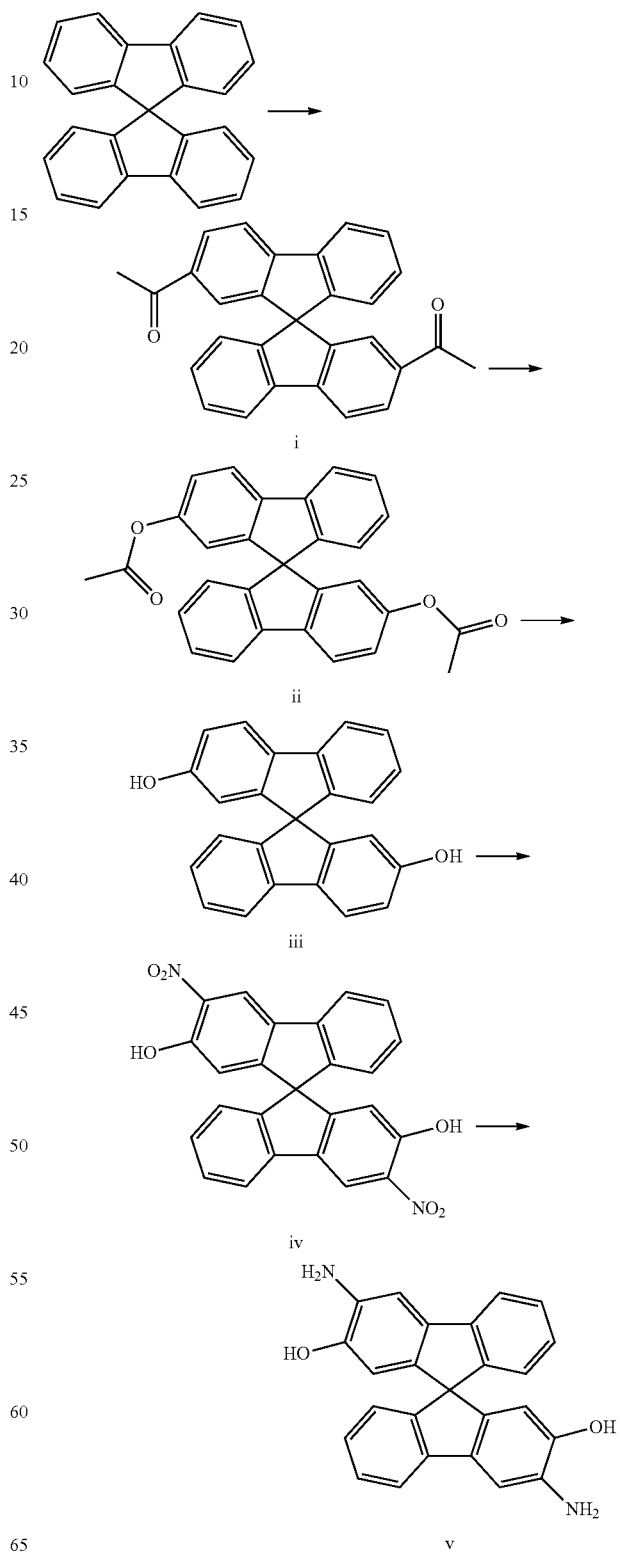

2,2'-Diacetyl-9,9'-spirobifluorene (i)

Aluminum trichloride (12.6 g, 94.5 mmol) and acetic chloride (6.20 g, 79.0 mmol) were dissolved in 200 mL dichloromethane at 0° C. To it, 9,9'-spirobifluorene (10.0 g, 31.6 mmol) dissolved in 60 mL dichloromethane was added dropwise over 2 hrs. The reaction system was stirred overnight and then poured into ice water (300 mL). The organic phase was separated and washed with saturated $K_2CO_3$ (aq) and water, then dried with magnesium sulfate. The solvent of the organic phase was removed by rota-evaporation. An off-white solid (9.0 g, yield: 71%) was obtained after column chromatography. $^1$H NMR (CDCl$_3$, 400 MHz): δ 8.09 (d, 2H, J=8.04 Hz), 7.95-7.99 (m, 4H), 7.45 (t, 2H, J=7.44 Hz, 7.44 Hz), 7.34 (s, 2H), 7.21 (t, 2H, J=7.48 Hz, 7.48 Hz), 6.76 (d, 2H, J=7.6 Hz), 2.52 (s, 6H).

2,2'-Diacetyloxy-9,9-spirobifluorene (ii)

2,2'-Diacetyl-9,9'-bispirofluorene (4.08 g, 10.0 mmol) and meta-chloroperoxybezoic acid (70%, 6.71 g, 27.3 mmol) were dissolved in 240 mL dichloromethane. The system was stirred at room temperature for 10 hrs and then heated to reflux for another 10 hrs. The organic phase was washed with saturated $K_2CO_3$ solution, and then water, which was further dried with magnesium sulfate. The solvent of the organic phase was removed by rota-evaporation and an off-white product (3.50 g, yield: 81%) was obtained after column chromatography. TLC: dichloromethane, $R_f$=0.75; $^1$H NMR (400 MHz, CDCl$_3$): δ 7.85 (t, 4H, J=8.44 Hz), 7.41 (t, 2H, J=7.44 Hz), 7.14-7.20 (m, 4H), 6.80 (d, 2H, J=7.6 Hz), 6.52 (d, 2H, J=2.04 Hz), 2.21 (s, 6H).

2,2'-Dihydroxide-9,9'-spirobifluorene (iii)

2,2'-Diacetyloxy-9,9-spirobifluorene (8.40 g, 19.4 mmol) was dissolved in 300 mL methanol. To it, aqueous NaOH solution (1.68 g, 42.0 mmol) dissolved in water (56 mL) was added dropwise. The reaction was stirred under $N_2$ overnight at room temperature, and thereafter, HCl (2 N, 30 mL) was added to neutralize the reaction. Most of the methanol was removed by rota-evaporation. The water phase was extracted with ethyl acetate (3×50 mL) and dried with magnesium sulfate. The solvent was removed and the pure off-white solid product (6.00 g, yield: 88.7%) was obtained after recrystallization from ethyl acetate/ligroin mixed solvent. TLC: ethyl acetate/ligroin=1/1, $R_f$=0.5; $^1$H NMR (400 MHz, CDCl$_3$): δ 7.72-7.79 (m, 4H), 7.38 (t, 2H, J=8.0 Hz, 8.0 Hz), 7.10 (t, 2H, J=8.0 Hz, 8.0 Hz), 6.87-6.90 (m, 2H), 6.87-6.90 (d, 2H, J=8.0 Hz), 6.24 (s, 2H).

3,3'-Dinitrol-2,2'-dihydroxyl-9.9'-spirobifluorene (iv)

2,2'-Dihydroxide-9,9'-spirobifluorene (696 mg, 2.00 mmol) was dissolved in 20 mL acetic acid. To it, $HNO_3$ (4 N, 1.10 mL) was added dropwise over half an hour. The system was stirred overnight, filtrated, and a yellow powder (580 mg, yield: 66.2%) as a mixture of isomers was obtained. The symmetric isomer product was obtained after column separation as a light yellow solid (320 mg, yield: 36.5%). TLC: Dichloromethane/ligroin=1/1, $R_f$=0.35. $^1$H NMR (400 MHz, CDCl$_3$): δ 10.75 (s, 2H), 8.54 (s, 2H), 7.87 (d, 2H, J=7.72 Hz), 7.45 (t, 2H, J=7.56 Hz, 7.56 Hz), 7.20 (t, 2H, J=7.54 Hz, 7.54 Hz), 6.75 (d, 2H, J=7.64 Hz), 6.50 (s, 2H). $^{13}$C NMR (100 MHz, CDCl$_3$): δ 158.40, 155.72, 146.97, 139.18, 134.43, 133.81, 129.13, 129.01, 124.38, 120.54, 116.12, 115.48, 65.77.

3,3'-Diamino-2,2'-dihydroxyl-9.9'-spirobifluorene (v)

3,3'-dinitrol-2, 2'-dihydroxyl-9.9'-spirobifluorene (1.31 g, 3.0 mmol) was dissolved in THF and DMF (15/15 mL) mixed solvent. To it, palladium on carbon (0.5 g, 10%) was added in one portion under $N_2$ atmosphere. $H_2$ up to 1.5 Mpa was added into the system in an autoclave. Thereafter, the reaction was heated to 40° C. for 24 hrs, cooled to room temperature, filtered through celite, and then washed with DMF (10 mL) for 3 times before being dropped into hexane/dichloromethane (200 mL/100 mL) mixed solvent. The precipitate was filtered and dried. The pure monomer (1.07 g, yield 90%) can be obtained by vacuum sublimation. $^1$H NMR (400 MHz, DMSO-d$_6$): δ9.00 (s, 2H), 7.60 (d, 2H, J=7.52 Hz), 7.22 (t, 2H, J=7.44 Hz, 7.44 Hz), 7.09 (s, 2H), 6.92 (t, 2H, J=7.44 Hz, 7.44 Hz), 6.47 (d, 2H, J=7.52 Hz), 5.93 (s, 2H), 4.60 (s, 4H). $^{13}$C NMR (100 MHz, DMSO-d$_6$): δ149.9, 145.2, 142.8, 138.0, 137.0, 132.8, 127.7, 126.0, 123.4, 118.8, 109.6, 105.8, 64.9. HRMS (ESI): for $C_{25}H_{19}N_2O_2^+$ [M+H]$^+$, 379.1441, found, 379.1428. Anal. Calcd. for $C_{25}H_{18}N_2O_2$: C, 79.35; H, 4.79; N, 7.40. Found: C, 79.14; H, 4.11; N, 8.55.

Synthesis of 6FDA-HSBF 3,3'-diamino-2,2'-dihydroxyl-9,9'-spirobifluorene (iv) (378.1 mg, 1.00 mmol) and 6FDA (444.4 mg, 1.00 mmol) were added to m-cresol (5.0 mL). The reaction system was stirred at 60° C. for 1 hr to form a clear solution. Isoquinoline (3 drops) was added, the system was then heated gradually to 180° C. and kept for 8 hrs, then poured into methanol. The remaining m-cresol was extracted with methanol using a Soxhlet extractor. A pale yellow polymer (750 mg, yield: 95%) was obtained by dissolving in THF and reprecipitation in methanol twice. $^1$H NMR (400 MHz, DMSO-d$_6$): δ10.0 (s, 2H), 8.25 (d, 2H, J=7.64 Hz), 8.04 (s, 2H), 8.00 (s, 2H), 7.88 (s, 4H), 7.44 (s, 2H), 7.16 (s, 2H), 6.77 (s, 2H), 6.32 (s, 2H). FT-IR (polymer film, v, cm$^{-1}$): 3200~3500 (s, br, —OH), 3025 (s, m, C—H), 2920 (s, m, C—H), 1715 (s, str, imide), 1200-1420 (m, str, ph). Anal. Calcd. C, 67.01; H, 2.81; N, 3.55. Found: C, 64.22; H, 3.22; N, 3.20. Molecular weight: $M_n$=2.89×10$^4$, PDI=2.41. $S_{BET}$=70 m$^2$/g.

Synthesis of SPDA-HSBF

The procedure for the synthesis SPDA-HSBF was the same as described for 6FDA-HSBF. The SPDA was used as monomer and the polymer SPDA-HSBF was obtained as a yellow filament. $^1$H NMR (400 MHz, DMSO-d$_6$): δ 9.94 (s, 2H), 8.54 (s, 2H), 7.74-7.90 (m, 4H), 7.48 (d, 2H, J=2.72 Hz), 7.36 (d, 2H, J=3.2 Hz), 6.98-7.09 (m, 4H), 6.54-6.70 (m, 4H), 6.05-6.37 (m, 4H), 2.30 (s, 2H), 2.14 (s, 2H), 1.21-1.37 (m, 12H). FT-IR (polymer film, v, cm$^{-1}$): 3200~3500 (s, br, —OH), 3025 (s, m, C—H), 2920 (s, m, C—H), 1715 (s, str, imide), 1200-1420 (m, str, ph). Anal. Calcd. C, 76.53; H, 4.14; N, 2.88. Found: C, 74.10; H, 4.29; N, 2.78. Molecular weight: $M_n$=4.24×10$^4$, PDI=2.30. $S_{BET}$=464 m$^2$/g.

Example 2: Synthesis of the Monomer
9,10-dimethyl-2,6-dihydroxy-3,7-diaminotriptycene Scheme S2: Synthesis of the triptycene-based dihydroxy diamines.

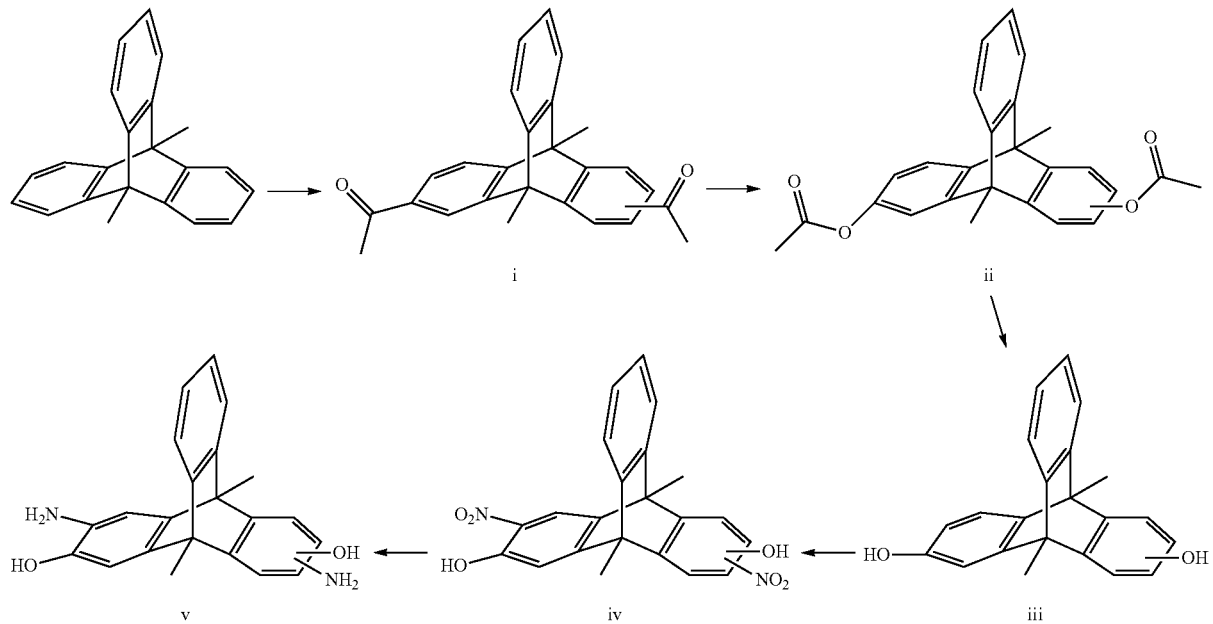

9,10-dimethyl-2,6(7)-diacetyltriptycene (i)

9,10-dimethyltriptycene (1.121 g, 4.00 mmol) and acetyl chloride (0.660 g, 8.40 mmol) were dissolved in anhydrous dichloromethane (30 mL) and cooled in an ice bath. To it, anhydrous AlCl$_3$ (1.335 g, 10.0 mmol) was added in portions. After the addition, the ice-bath was removed and the reaction was further stirred at room temperature for another 2 hrs and then poured into ice. The organic phase was separated and washed with brine, water, and dried with magnesium sulfate. The pure product (512 mg, yield: 35%) was obtained after column chromatography. TLC: Dichloromethane, R$_f$=0.4 (2,6-substituted), 0.32 (2, 7-substituted); $^1$H NMR (400 MHz, CDCl$_3$): δ 8.02 (d, 2H, J=1.6 Hz), 7.73 (dd, 2H, J=7.84 Hz, 1.6 Hz), 7.49-7.51 (m, 2H), 7.44-7.46 (m, 2H), 7.12-7.14 (m, 2H), 2.59 (s, 6H), 2.56 (s, 6H).

9,10-dimethyl-triptycenyl-2,6 (7)-diacetatyloxytriptycene (ii)

The intermediate i (480 mg, 1.4 mmol) and m-CPBA (2.24 g, 1.40 mmol) were dissolved in 30 mL chloroform. The reaction was then refluxed for 2 hrs and then poured into 100 mL water. The organic phase was washed in sequence with saturated sodium carbonate (aq), then water, and finally dried with magnesium sulfate. The solvent of the organic phase was removed by rota-evaporation and the product (500 mg, yield: 90%) was obtained after column separation. TLC: Dichloromethane, R$_f$=0.6; $^1$H NMR (400 MHz, CDCl$_3$): δ 7.34-7.38 (m, 4H), 7.07-7.09 (m, 4H), 6.76-6.79 (dd, 2H, J=8.1 Hz, 2.2 Hz), 2.40 (s, 6H), 2.30 (s, 6H).

9,10-dimethyl-2,6(7)-dihydroxytriptycene (iii)

The intermediate ii (530 mg, 1.33 mmol) was dissolved in ethanol (30 mL). To it, KOH (201 mg, 3.5 mmol) dissolved in 5 mL water was added dropwise. The resulting solution was stirred for half an hour and then poured into water (100 mL). HCl (2N, 5 mL) was added and a white precipitate was formed and subsequently filtrated. The product (355 mg, 85% yield) was obtained by recrystallization from ethanol/water mixed solvent. TLC: dichloromethane/ethyl acetate=10/1, R$_f$=0.2; $^1$H NMR (500 MHz, DMSO-d$_6$): δ 9.16 (s, 2H), 7.26-7.28 (m, 2H), 7.06 (d, 2H, J=6.7 Hz), 6.98-6.99 (m, 2H), 6.73 (d, 2H, J=1.9 Hz), 6.33 (dd, 2H, J=6.7 Hz, 1.9 Hz), 2.18 (s, 6H).

9,10-dimethyl-3,7(6)-dinitrol-2,6(7)-dihydroxytriptycene (iv)

The intermediate iii (1.75 g, 5.57 mmol) was added to HAc (100 mL). To it, diluted HNO$_3$ (4N, 2.9 mL) was added dropwise. The solution was stirred for another 4 hrs, and then poured into water (200 mL). Filtrated and the pure 9,10-dimethyl-3,7 (6)-dinitrol-2,6 (7)-dihydroxytriptycene (0.90 g, 40% yield) was obtained after column separation. TLC: Dichloromethane, R$_f$=0.85; $^1$H NMR (400 MHz, CDCl$_3$): δ 10.84 (s, 2H), 8.03 (s, 2H), 7.43-7.45 (dd, 2H, J=8.8 Hz, 3.2 Hz), 7.21 (dd, 2H, J=8.8 Hz, 3.2 Hz), 7.18 (s, 2H), 2.46 (s, 6H).

9,10-dimethyl-2,6 (7)-dihydroxy-3,7(6)-diaminotriptycene (v)

The intermediate iv (500 mg, 1.24 mmol) and Pd/C (10%, 0.1 g) were added to ethanol (100 mL) under N$_2$. To it, hydrazine monohydrate (64%, 1.0 mL) was added dropwise. The reaction system was thereafter heated to reflux for 1 hr, then cooled to room temperature and filtrated through celite to water (300 mL). Finally, microcrystals were obtained (300 mg, 51% yield) and dried under vacuum at 70° C. for 24 hrs. TLC: Ethyl acetate, $R_f$=0.25; $^1$H NMR (500 MHz, DMSO-d$_6$): δ 8.63 (s, 2H), 7.16 (s, 2H), 6.90 (s, 2H), 6.60 (s, 2H), 6.57 (s, 2H), 4.23 (s, 4H), 2.05 (s, 6H).

Example 3: Synthesis of the Polymer 6FDA-HMTA

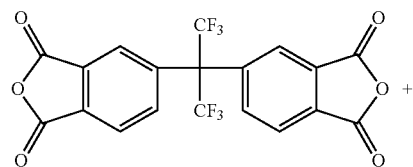

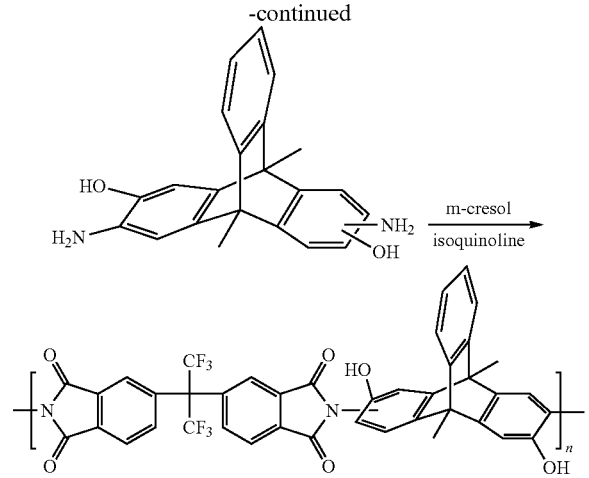

9,10-dimethyl-2,6-dihydroxy-3,7(6)-diaminotriptycene (180 mg, 0.5 mmol) and 6FDA (222.2 mg, 0.5 mmol) were added to m-cresol (2.0 mL). The reaction mixture was heated to 60° C. under N$_2$ for 1 hr to form a clear solution. Isoquinoline (2 drops) was added and the system was heated to 120° C. for 2 hrs, then 180° C. for 3 hrs before cooling to room temperature. The solution was poured into methanol, filtrated and reprecipitated in water. 0.38 g (yield 96.4%) of off-white polymer was obtained after drying in vacuum oven at 120° C. for 24 hrs. $^1$H NMR (400 MHz, DMSO-d$_6$): δ 9.70 (s, 2H), 8.15 (s, 2H), 8.00 (s, 2H), 7.71 (s, 2H), 7.41 (s, 2H), 7.30 (s, 2H), 7.11 (s, 2H), 2.24 (s, 6H).). FT-IR (polymer film, v, cm$^{-1}$): 3200~3500 (s, br, —OH), 2973 (s, m, C—H), 1711 (s, str, imide), 1200-1420 (m, str, ph). Anal. Calcd. C, 76.53; H, 4.14; N, 2.88. Found: C, 74.10; H, 4.29; N, 2.78. Molecular weight: $M_n$=3.05×10$^4$, PDI=2.67. $S_{BET}$=80 m$^2$/g. $T_d$=460° C.

Example 4: Synthesis of the Polymer SFDA-HMTA

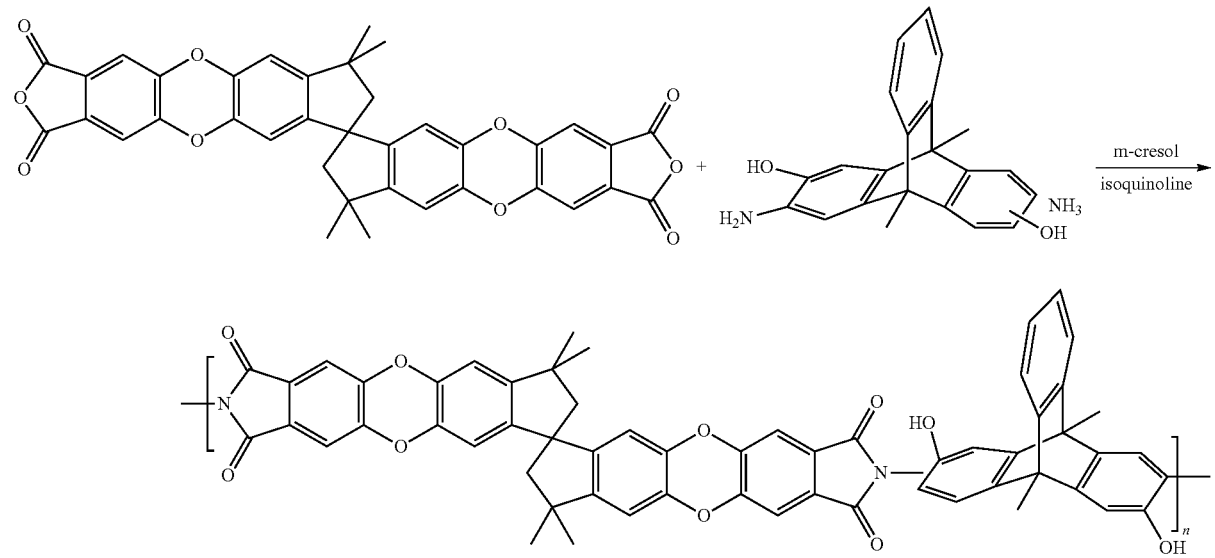

The synthetic procedure was the same as that of 6FDA-HMTA; the polymer was obtained as a yellow powder with a yield of 95%. $^1$H NMR (400 MHz, DMSO-d$_6$): δ 9.75 (s, 2H), 7.40-7.47 (m, 6H), 7.00-7.22 (m, 8H), 6.48 (s, 2H), 2.38 (s, 4H), 1.30-1.38 (m, 12H). FT-IR (polymer film, v, cm$^{-1}$): 3200~3500 (s, br, —OH), 2948 (s, m, C—H), 1718 (s, str, imide), 1200-1420 (m, str, ph). Anal. Calcd. C, 76.53; H, 4.14; N, 2.88. Found: C, 74.10; H, 4.29; N, 2.78. Molecular weight: $M_n$=2.19×10$^4$, PDI=1.96. $_{BET}$=450 m$^2$/g. $T_d$=470° C.

Example 5

A 6FDA-HSBF film with thickness of 80~100 micron was made by casting a 3 wt % (wt/v) of polymer in THF in a flat Petri dish. The solvent was evaporated over a period of 2 days at room temperature and then for 24 hours at 250° C. in a vacuum oven. The gas permeation properties of the resulting film were determined with a constant volume/variable pressure technique. The tests were performed at a feed pressure of 2 atm at 35° C. The results are summarized in Table 1.

TABLE 1

| Permeability and selectivity of 6FDA-HSBF for different gases at 35° C. | | | | | | | | |
|---|---|---|---|---|---|---|---|---|
| | Permeability (Barrer) | | | | | Ideal selectivity ($\alpha_{X/Y}$) | | |
| Polymer | $H_2$ | $N_2$ | $O_2$ | $CH_4$ | $CO_2$ | $H_2/N_2$ | $O_2/N_2$ | $CO_2/N_2$ | $CO_2/CH_4$ |
| 6FDA-HSBF | 162 | 3.8 | 19.3 | 2.4 | 100 | 42.5 | 5.1 | 26.3 | 41.7 |

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim at least the following:

1. A composition, comprising:
an o-hydroxy-functionalized diamine having the following structure:

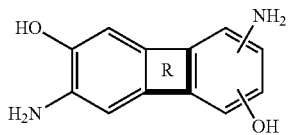

wherein R is selected from the following structures:

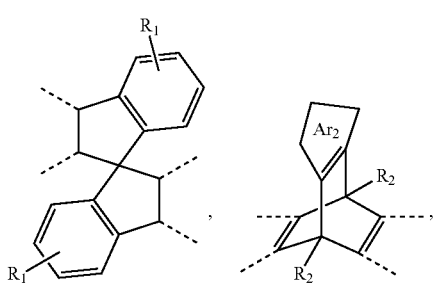

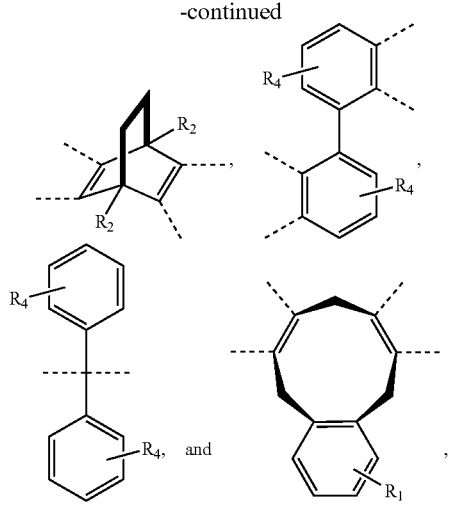

wherein $R_1$ is H or a substituted or unsubstituted linear alkyl group, wherein each $R_2$ and $R_4$ are independently selected from the group consisting of: H and a linear or branched, substituted or unsubstituted, alkyl group, wherein $Ar_2$ is selected from the group consisting of: an aryl group and a heteroaryl group where each are substituted or unsubstituted.

2. The composition of claim 1, wherein R is

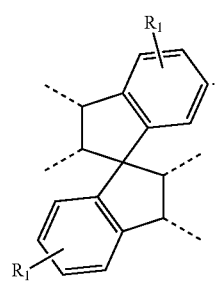

and $R_1$ is H.

3. The composition of claim 1, wherein R is

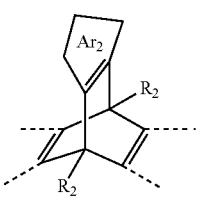

4. The composition of claim 1, wherein R is

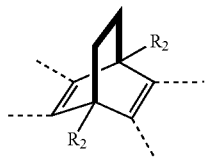

5. The composition of claim 1, wherein R is

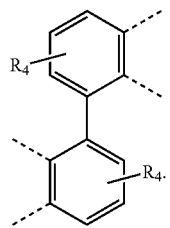

6. The composition of claim 1, wherein R is

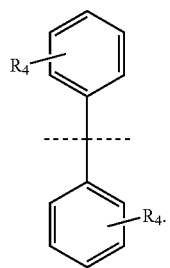

7. The composition of claim 1, wherein R is

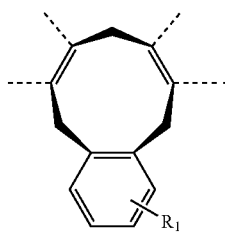

8. A composition, comprising:
a polyimide having the following structure:

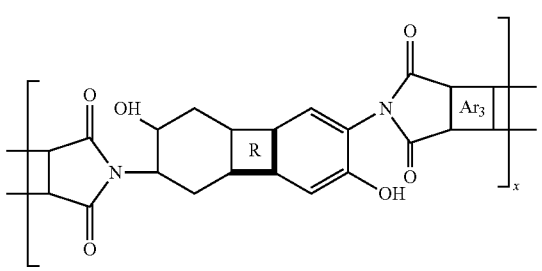

wherein $Ar_3$ is an aryl group or a heteroaryl group, wherein x is 1 to 100,000, wherein R is selected from the following structures:

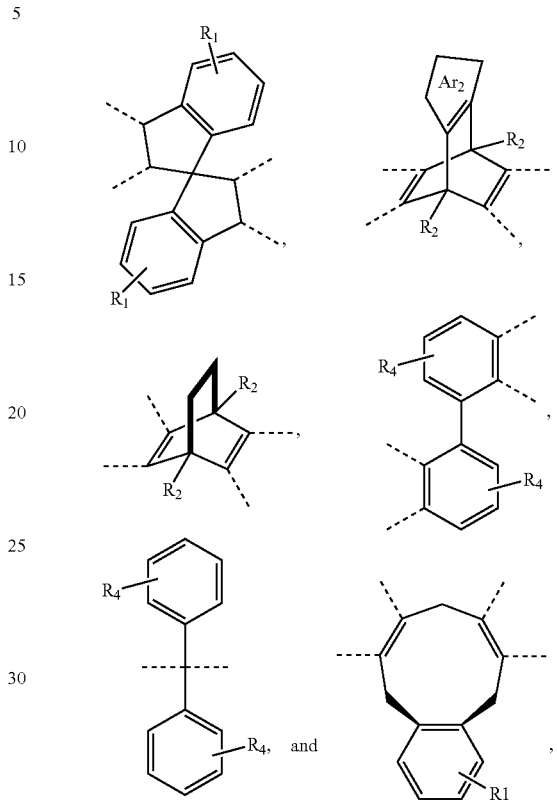

wherein $R_1$ is H or a substituted or unsubstituted linear alkyl group wherein, each of $R_2$ and $R_4$ are independently selected from the group consisting of: H and a linear or branched, substituted or unsubstituted, alkyl group, wherein $Ar_2$ is selected from the group consisting of: an aryl group and a heteroaryl group where each are substituted or unsubstituted.

9. The composition of claim 8, wherein R is

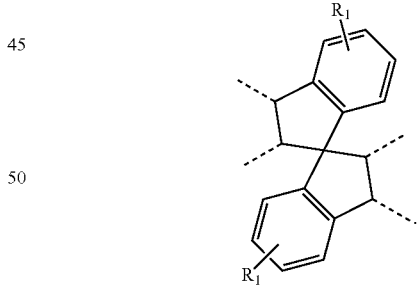

and $R_1$ is H.

10. The composition of claim 8, wherein R is

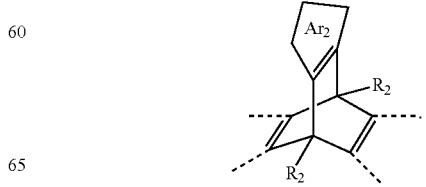

11. The composition of claim 8, wherein R is

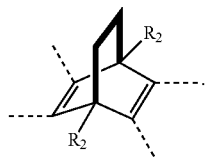

12. The composition of claim 8, wherein R is

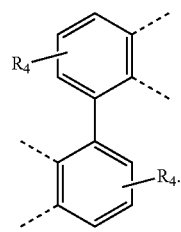

13. The composition of claim 8, wherein R is

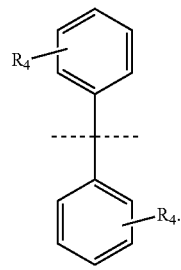

14. The composition of claim 8, wherein R is

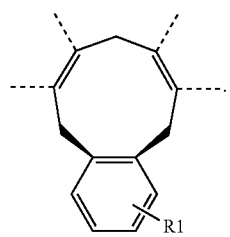

15. A method of making an aromatic diamine, comprising:

wherein A includes acetylation of the bulky starting structures by Friedel-Crafts reaction, wherein B includes transferring the diacetyl intermediate to diester via Baeyer-Villiger oxidation reaction, wherein C includes the hydrolysis of the diester, wherein D includes the nitration of the diphenol intermediate, wherein E includes the reduction of the ortho-diphenol-dinitrol intermediate to the corresponding ortho-hydroxy-functionalized diamine, wherein R is selected from the following structures:

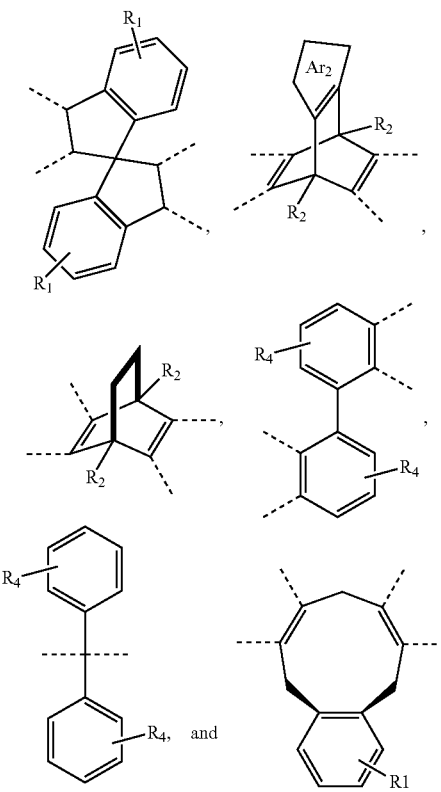

wherein $R_1$, $R_2$, and $R_4$ are independently a linear or branched, substituted or unsubstituted alkyl group, wherein $Ar_2$ is selected from the group consisting of: an aryl group and a heteroaryl group where each is substituted or unsubstituted.

16. A method for making a polyimide, comprising: reacting a dianhydride with an o-hydroxy-functionalized diamine

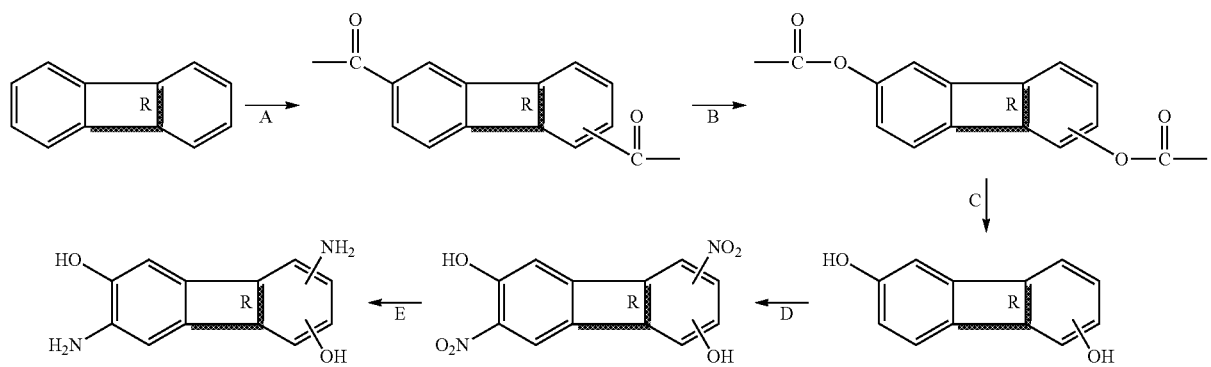

to form a polyimide, wherein the o-hydroxy-functionalized diamine has the following structure:

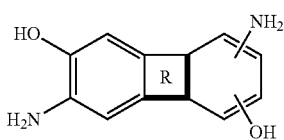

wherein R is selected from the following structures:

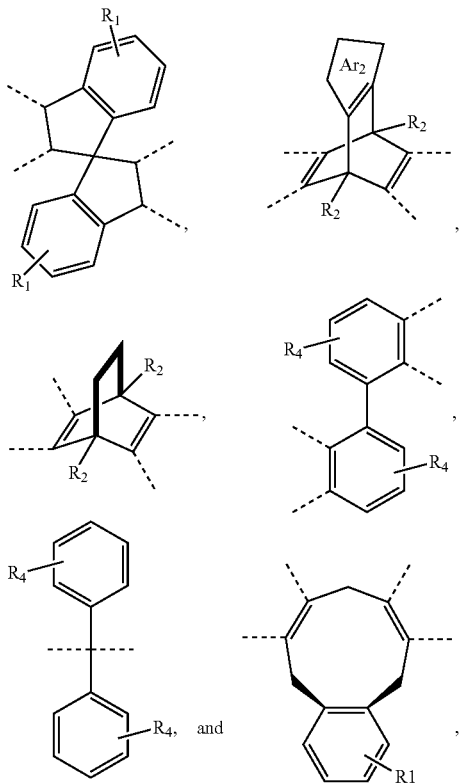

wherein $R_1$ is H or a substituted or unsubstituted linear alkyl group, wherein each of $R_2$ and $R_4$ are independently selected from the group consisting of: H and a linear or branched, substituted or unsubstituted, alkyl group, wherein $Ar_2$ is selected from the group consisting of: an aryl group and a heteroaryl group where each are substituted or unsubstituted.

17. A membrane, comprising: a polyimide having the following structure:

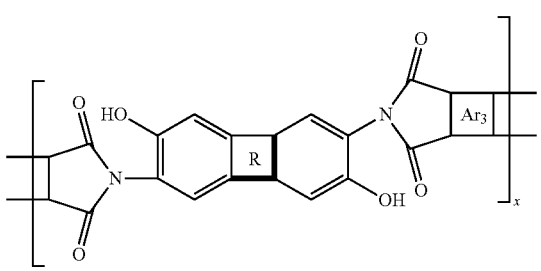

wherein $Ar_3$ is selected from an aryl group or a heteroaryl group, wherein x is 1 to 100,000, wherein R is selected from the following structures:

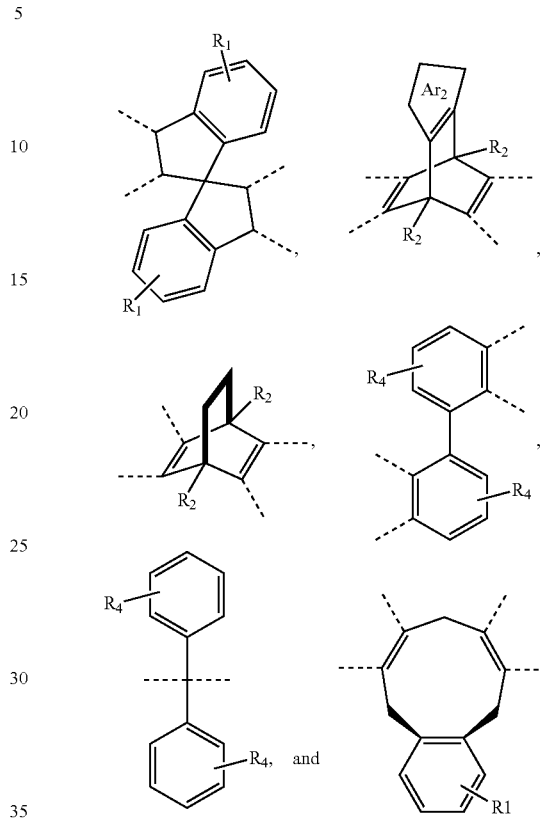

wherein $R_1$ is H or a substituted or unsubstituted linear alkyl group wherein, each of $R_2$ and $R_4$ are independently selected from the group consisting of: H and a linear or branched, substituted or unsubstituted, alkyl group, wherein $Ar_2$ is selected from the group consisting of: an aryl group and a heteroaryl group where each can be substituted or unsubstituted.

18. A method of separating a gas from a gas mixture, comprising: separating a first gas from a first gas mixture containing at least a second gas with a membrane to form a second gas mixture that is enriched in at least one gas component of the first mixture, wherein the membrane includes a polyimide having the following structure:

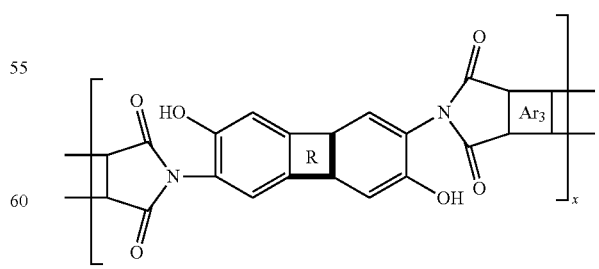

wherein $Ar_3$ is selected from an aryl group or a heteroaryl group, wherein x is 1 to 100,000, wherein R is selected from the following structures:

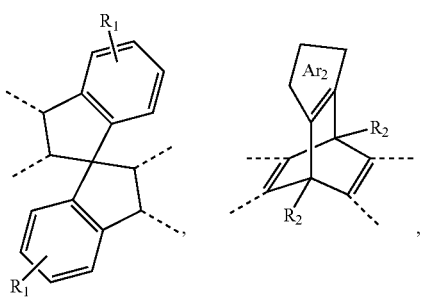
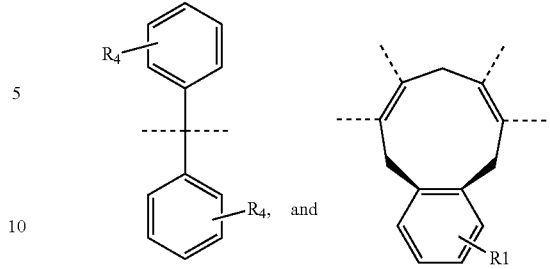
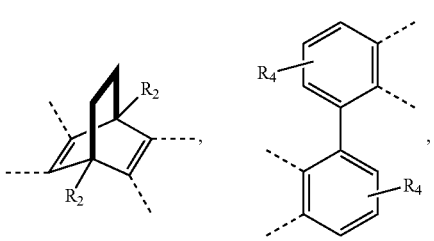

wherein $R_1$ is H or a substituted or unsubstituted linear alkyl group wherein, each of $R_2$ and $R_4$ are independently selected from the group consisting of: H and a linear or branched, substituted or unsubstituted, alkyl group, wherein $Ar_2$ is selected from the group consisting of: an aryl group and a heteroaryl group where each are substituted or unsubstituted.

19. The method of claim 18, wherein the first gas is selected from the group consisting of: He, $H_2$, $CO_2$, $H_2S$, $H_2O$, $O_2$, $C_2H_4$, $C_3H_6$, and a combination thereof, and wherein the second gas is $N_2$, Ar, $CH_4$, Co, saturated $C_{2+}$ hydrocarbons or a combination thereof.

* * * * *